United States Patent [19]
Khawli et al.

[11] Patent Number: 5,194,594
[45] Date of Patent: Mar. 16, 1993

[54] MODIFIED ANTIBODIES

[75] Inventors: Leslie A. Khawli, Diamond Bar; Alan L. Epstein, La Canada, both of Calif.

[73] Assignee: Techniclone, Inc., Tustin, Calif.

[21] Appl. No.: 579,375

[22] Filed: Sep. 7, 1990

[51] Int. Cl.$^5$ .................. C07K 15/28; C07K 17/06; A61K 49/02
[52] U.S. Cl. .................. 530/391.5; 530/391.1; 530/391.3; 530/391.7; 530/391.9; 424/1.1; 424/9; 424/85.91
[58] Field of Search .............. 530/389, 390, 391, 391.1, 530/391.3, 391.5, 391.7, 391.9; 424/1.1, 9, 85.91

[56] References Cited

U.S. PATENT DOCUMENTS

| | | | |
|---|---|---|---|
| 4,676,980 | 6/1987 | Segal et al. | 424/85.91 |
| 4,698,320 | 10/1987 | Urnmovitz | 530/387 |
| 4,724,213 | 2/1988 | Epstein | 435/240.27 |
| 4,771,128 | 9/1988 | Ferris et al. | 530/417 |
| 4,831,122 | 5/1989 | Buchsbaum et al. | 530/391.3 |
| 5,011,676 | 4/1991 | Thakun | 424/1.1 |
| 5,019,393 | 5/1991 | Ito et al. | 424/423 |
| 5,043,340 | 8/1991 | Cullinan | 514/283 |

FOREIGN PATENT DOCUMENTS

| | | |
|---|---|---|
| 0196669 | 10/1986 | European Pat. Off. |
| 308208 | 3/1989 | European Pat. Off. |
| 0350230 | 1/1990 | European Pat. Off. |
| 0384624 | 8/1990 | European Pat. Off. |
| 9102541 | 3/1991 | PCT Int'l Appl. |
| 8605098 | 9/1986 | World Int. Prop. O. |

OTHER PUBLICATIONS

Colcher et al., (1981) PNAS 78(5): 3199-3203.
Pelham et al., (1983) Cancer Immunol Immunotha 15:210-216.
Srinivasachar et al., (1989) Biochemistry 28(6) 2501-2509.
Blair (1983) J. Immunol. Methods 59:129-143.
Jung et al., (1981) Biochem. Biophys Res. Commun. 101(2): 599-606.
Lin et al, (1985) PNAS USA 82:8648-8652.
Wawrynczak et al., (1987) in Immununconyate Antibody Coyngates in Radioniginet Therapy of Cancer, CW Vogeled NY Oxford Univ. Press pp. 28-55.
"Macromolecular Photoaffinity Labeling with Radioactive Photoactivable Heterobifunctional Reagents", by Tae H. Ji, et al., Analytical Bioch. 121:286-289 (1982).
"Addition of Sulfhydryl Groups to Escherichia coli Ribosomes by Protein Modification with 2-Iminothiolane", by Rodney Jue, et al., Bioch. 17:5399-5405 (1978).
"Photoactivated Heterobifunctional Cross-Linking Reagents Which Demonstrate the Aggregation State of Phospholipase A2", by Randolph V. Lewis, et al., Bioch. 16:5650-5654 (1977).
"Synthesis and Application of Cleavable Photoactivable Heterobifunctional Reagents", by Elio F. Vannin, et al., Biochemistry 20:6754-6760 (1981).
"Localization of Mammary Tumors in Vivo with 1-Labeled FAb Frangments of Antibodies Against Mouse Mammary Epithelial (MME) Antigens", by T. Wilbanks, et al., Cancer 48:1768-1775 (1981).
"Biological Response Modifiers: The New Immunotherapy", by Kenneth A. Foon, Cancer Res. 49:1621-1639 (1989).

(List continued on next page.)

*Primary Examiner*—Christine M. Nucker
*Assistant Examiner*—Kay K. Kim
*Attorney, Agent, or Firm*—Knobbe Martens Olson & Bear

[57] ABSTRACT

Modified antibodies are disclosed which have been modified by chemical conjugation with a heterobifunctional reagent, such as SPDP. The use of these modified antibodies in the diagnosis and therapy of cancer and other mammalian disease is also disclosed. Diagnostic uses include immunoscintography. The modified antibodies may be further conjugated with labels or biologically active molecules for use in such diagnosis and therapy. The modified antibodies may also be formulated into pharmaceutical compositions for these purposes.

13 Claims, 16 Drawing Sheets

OTHER PUBLICATIONS

"Improved Radioimaging and Tumor Localization with Monoclonal F(ab')2" by Richard L. Wahl, et al., J. Nucl. Med." 24:316–325 (1983).

"Cleavage of Structural Proteins during the Assembly of the Head of Bacteriophage T4", by U. K. Laemmli, Nature 227:680–685 (1970).

"Two New Monoclonal Antibodies, Lym-1 and Lym-2, Ractive with Human B-Lymphocytes and Derived Tumors, with Immunodiagnostic and Immunotherapeutic Potential", by Alan L. Epstein, et al., Cancer Res. 47:830–840 (1987).

"Determination of Sulfhydryl Groups with 2,2'-or 4,4'-Dithiodipyridine", by D. R. Grassetti, et al., Arch. Bioch. Biophys. 119:41–49 (1967).

"Protein Thiolation and Reversible Protein–Protein Conjugation", by Jan Carlsson, et al., Biochem. J. 173:723–737 (1978).

"On the Fragmentation of Monoclonal IgG1, IgG2a, and IgG2a, and IgG2b from BALB/c MICE", by Peter Parham J. Immuno 131:2895–2902 (1983).

"I Radiolabeling of Monoclonal Antibodies for In Vivo Procedures", by Stanley L. Mills, et al., Hybridoma 5:265–275 (1986).

Change in Binding Reactivity of an Anti-Tumor Monoclonal Antibody After the Introduction of 2-Pyridly Disulphide Groups, Hybridoma 5:1–8 (1986).

National Library of Medicine, Database Medline, accession no. 89048210, Brown BA: "Conjugation of metallothionein to a murine monoclonal antibody", Anal Biochem. 1988 Jul.:172(1): 22–8.

Cancer Research, vol. 47, 1987, P. E. Thorpe et al.: "New coupling agents for the synthesis of immunotoxins containing a hindered disulfide bond with improved stability in vivo", see p. 5924–p. 5931, p. 5927, Results and p. 5929–30.

Cancer Immunol Immunother, vol. 31, 1990, M. A. Winkler et al.: "Biodistribution and plasma survival in mice of anti-melanoma monoclonal antibody–cross-–linked to OKT3", see pp. 278–284, p. 282–283.

Biochemistry, vol. 17, No. 8, 1978, Te Piao King et al.: "Preparation of protein conjugates via intermolecular disulfide bond formation", see page 1499–p. 1506, p. 1505.

The Journal of Immunology, vol. 141, No. 10, 1988, M. J. Glennie et al.: "Bispecific F(AB'y)2 antibody for the delivery of saporin in the treatment of lymphoma", see pp. 3662–3670; p. 3665, left column first paragraph and p. 3663, right column.

National Library of Medicine, Database Medline, NLM accession No. 88060540, Koizumi M: "Preparation of 67Ga-labeled antibodies using deferoxamine as a bifunctional chelate". An improved method:, J. Immunol. Methods 1987 Nov. 23; 104(1–2); 93–102.

Image obtained on day 7 after injection of I-131 labeled intact Lym-1.
Region 1, whole mouse; Region 2, Raji tumor Image obtained on day 7 after injection
of I-131 labeled modified Lym-1.
Region 1, whole mouse; Region 2, Raji tumor Image obtained on day 7 after injection of I-131 labeled modified Lym-1.
Region 1, whole mouse; Region 2, Raji tumor Image obtained on day 5 after injection of I-131 labeled modified Lym-1.
Region 1, whole mouse; Region 2, Raji tumor Image obtained on day 1 after injection of I-131 labeled modified B72.3.
Region 1, whole mouse; Region 2, LS174T tumor Image obtained on day 4 after injection of I-131 labeled modified B72.3.
Region 1, whole mouse; Region 2, LS174T tumor

MODIFIED ANTIBODIES

BACKGROUND OF THE INVENTION

1. Field of the Invention

This present invention relates to modified antibodies. More specifically, the present invention relates to antibodies which have been modified by chemical conjugation with a heterobifunctional reagent and the use of these modified MAb's in the diagnosis and therapy of cancer and other mammalian disease.

2. Description of the Prior Art

The use of antibodies, particularly monoclonal antibodies ("MAb's"), has the potential to be an extremely valuable approach in the diagnosis and treatment of cancer. An important property of MAb's is their specificity for single antigens.

MAb's specific to tumor cell antigens have been produced. It has also been shown that MAb's may be efficiently coupled to adjuncts such as radionuclides. Such radio-labelled MAb's are useful in providing clinical data, such as tumor imaging from immunoscintography, also known as $\gamma$-camera imaging or radioimmunoimaging. In immunoscintography, the MAb's are allowed to bind to the specific tissue or tumor types having the antigen recognized by the MAb's. The radionuclides are then visualized through the use of appropriate technology, such as through the use of a germanium camera. It is the unique specificity of MAb's which enables their application in immunoscintography of tumors and other types of tissues.

However, the use of MAb's in immunoscintography has been limited due to high background levels and low binding capacity of the MAb's to their antigens. Experimental studies suggest that the biodistribution of radio-labelled MAb's is dependent on many factors, including the specificity and clearance time of the antibody. For effective diagnosis of a tumor through immunoscintography, an antibody should be selected which binds to an antigen which is dense and homogeneous on the tumor cell surface. Effective diagnosis through immunoscintography also requires that the antibody chosen should effectively bind to the tumor antigen. However, often MAb's which bind to appropriate antigens do not offer the required high binding affinity. Additionally, even the use of those MAb's which bind with high affinity relative to other MAb's may still produce a high level of non-specific binding, resulting in high background levels when used in immunoscintography. Thus, there is a need for a method of improving the effectiveness of binding of MAb's in order to improve immunoscintography as a diagnostic tool.

Additionally, the cytotoxic effect of MAb's can be markedly increased by coupling to radionuclides, drugs or toxins. The unique specificity of MAb's has raised hopes of the development of immunotherapy. In immunotherapy, biologically active agents are delivered using MAB's to particular undesirable cell types, such as tumor cells, thereby affecting the undesirable cell types without affecting other cells of the subject. However, immunotherapies require extremely high specificity antibodies in order to avoid affecting healthy tissue. Thus, a method of increasing the specificity of MAb's would be highly beneficial in achieving the goal of a safe, effective immunotherapy.

Many MAb's remain in the circulation for several days following introduction into a subject. This is undesirable for at least two reasons. One reason is that circulating MAb's produces high background levels in immunoscintography. A second reason is that circulating MAb's coupled to radionuclides or other potentially cytotoxic agents may produce undesirable side effects in the subject after prolonged exposure. Thus, there is a need for a method of decreasing the clearance time of MAb's. Of course, too great a decrease would result in MAb's being eliminated before any effective use of the MAb's could be made. Thus, there is a particular need for a method of decreasing the clearance time of MAb's without substantially affecting uptake of MAb's by tumor or other target tissue.

One factor which is critical in determining both the specificity and clearance time of an antibody is the form of the antibody. As used herein, an "intact" antibody molecule will refer to an unmodified antibody molecule comprised of two heavy chains and two light chains. The intact, whole antibody molecule is seen on the reactant side of the chemical equation of FIG. 1. As seen in FIG. 1, the intact molecule is divided into the $F_c$ and the $F_{ab}$ domains. $F(ab')_2$, the bivalent form of the $F_{ab}$ fragment, may be produced through the digestion of the $F_c$ domain with a protease.

The two heavy chains (designated as "H" in FIG. 1) are held together by one or more disulfide bridges. In intact molecules these disulfide bridges are normally protected from reducing agents. It has been found however, that removal of the $F_c$ domain allows facile reduction of the disulfide bridges. Thus, F(ab'), the monovalent form, may be produced from $F(ab')_2$ through the action of a mild reducing agent. Parham, P., On the Fragmentation of Monoclonal IgG1, IgG2a, and IgG2b from BALB/c Mice, *J. Immunol.* 131: 2895 (1983), the disclosure of which is hereby incorporated by reference, describes a method for the production of F(ab') and $F(ab')_2$. A schematic representation of the changes believed to occur in this method is shown by the chemical equation of FIG. 1.

$F_c$ has been found to be responsible for much of the non-specific binding of antibody molecules. It is also believed that the molecular weight of the fragments is below the threshold for glomerular filtration, thus allowing for rapid elimination of the fragments. Therefore, one approach to increasing clearance time of antibodies for use in radioimaging has been to break down intact antibody into various fragments, such as Fab and its divalent form, $F(ab')_2$. As expected, these fragments are cleared from the body so rapidly that their utility is reduced. Moreover, these fragments may result in reduced uptake by tumor or other target tissue relative to intact antibody. Thus, the although the use of these fragments in immunoscintography may provide better clearance and a higher target tissue to background ratios than with intact MAb's, the absolute concentration of MAb's in the target tissue containing the antigen to which the MAb's will bind has been found to be up to as many as three times or more as much with intact MAb's as with either of the fragments.

Furthermore, both types of fragments are removed from the blood stream very rapidly. Accordingly, the time of effectiveness for diagnostic or therapeutic techniques using these fragments is very short.

Heterobifunctional reagents are reagents having two groups capable of participating in different reaction. For example, succinimidyl 3-(2-pyridyldithio)propionate (SPDP) is heterobifunctional in that its N-hydroxysuccinimide ester group reacts with amino groups and the 2-pyridyl disulphide structure reacts with aliphatic thiols.

Orlandi et al., Change in Binding Reactivity of an Anti-Tumor Monoclonal Antibody After the Introduction of 2-Pyridyl Disulphide Groups, *Hybridoma* 5:1-8 (1986), reported that an increase in the in vitro binding of MAb's raised against human ovarian carcinoma could be obtained after chemical conjugation with the heterobifunctional reagent, SPDP.

The conjugated MAb's used by Orlandi et al. had on average, 11 PDP groups per molecule. Orlandi et al. found that the modified MAb's increase their binding activity in vitro to an extent that molecules not detected by the unmodified MAb's can be detected. These researchers reported no studies of the use of the conjugated MAb's in vivo. Additionally, these researchers believed that molecules having a very low number of antigenic sites were detected by the conjugated MAb's. Accordingly, the PDP modified MAb's had greatly reduced target-cell specificity relative to the unmodified counterparts.

Thus, despite the above advances, there remains a need for modified antibody fragments exhibiting greater specific activity to tumor antigens, allowing more absolute concentration of antibody to accumulate in tumor, and also having relatively rapid clearance time from the blood pool, yet not so rapid to reduce therapeutic or diagnostic effectiveness.

SUMMARY OF THE INVENTION

Figure 1:
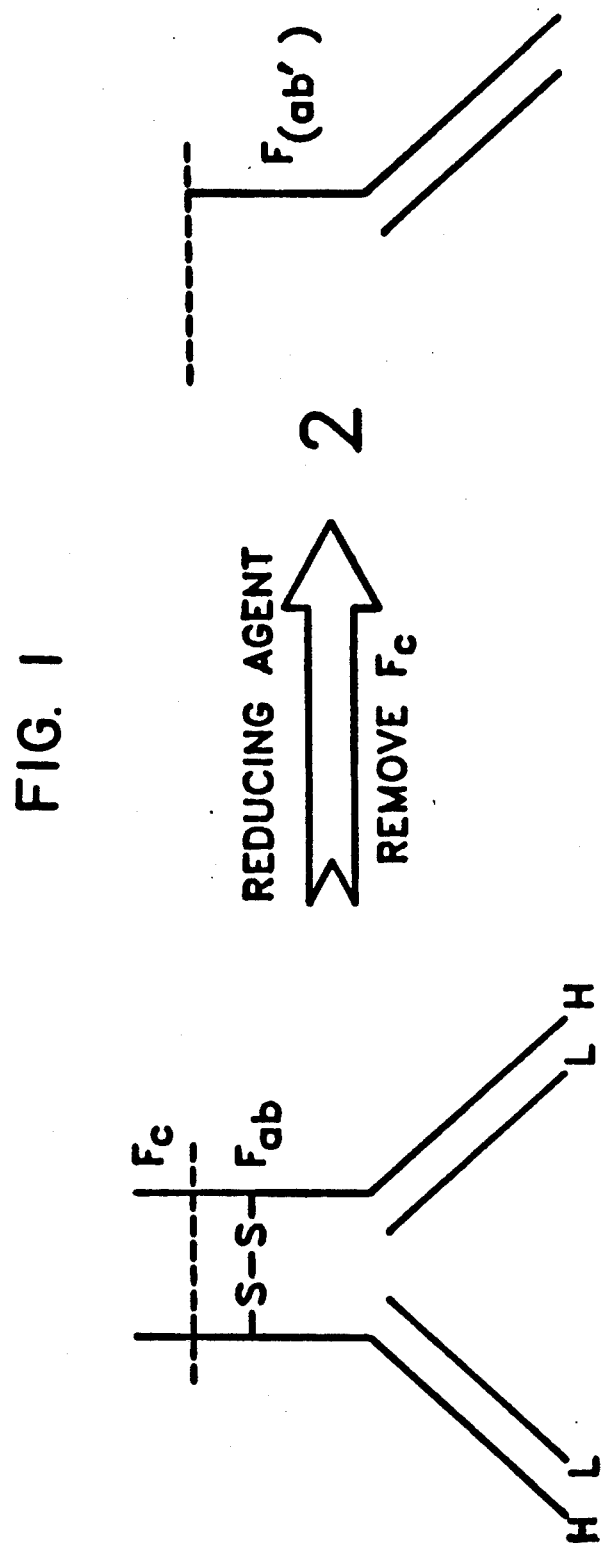
FIG. 1 shows a schematic representation of the believed to occur in a method of producing F(ab') and F(ab')$_2$ fragments.

The present invention provides antibodies chemically modified with a heterobifunctional reagent having an in vivo clearance rate between the clearance rates of F(ab')$_2$ fragments and intact antibodies of the same type. In a preferred embodiment, the heterobifunctional reagent is SPDP and the antibodies are selected from the group consisting of monoclonal antibodies, human antibodies, genetically engineered antibodies, chimeric antibodies, synthesized antibodies, and polyclonal antibodies.

The present invention also provides a method of imaging a specific tissue in a mammal comprising obtaining an antibody to the specific tissue, modifying the antibody by conjugation with a heterobifunctional reagent, introducing a label onto the antibody, introducing the antibody into the mammal and producing an image which reveals the label on said antibody. In a preferred embodiment, the antibody is modified by conjugation with an average of approximately one PDP group per antibody molecule and is labeled with a radionuclide which emits gamma radiation.

Additionally, the present invention provides a method of treating a disease state in mammal comprising obtaining an antibody specific to the diseased tissues in the mammal, modifying the antibody by chemical conjugation with a heterobifunctional reagent and with biologically active molecule, and administering the antibody to the mammal. In a preferred embodiment the antibodies are modified by chemical conjugation with, on average, one PDP group per antibody molecule and the biologically active molecule is selected from the group consisting of plant toxins, drugs, radionuclides and chelates.

The present invention also provides pharmaceutical compositions for use with the methods of the present invention. The compositions include a modified antibody in a pharmaceutically accepted carrier, excipient or base.

DETAILED DESCRIPTION OF THE INVENTION

We have discovered that modification of antibodies, including MAb's, human antibodies, genetically engineered antibodies, chimeric antibodies, synthesized antibodies and polyclonal antibodies, by conjugation with a heterobifunctional reagent, such as SPDP, leads to surprisingly enhanced accumulation of modified antibodies in target cells containing the antigen to which the antibodies will bind. Other heterobifunctional reagents, including sulfosuccinimidyl 2-(p-azido salicylamido-)ethyl-1,3'-dithiopropionate (SASD), sulfosuccinimidyl 2-(m-azido-o-nitrobenzamido)-ethyl-1,3'-dithiopropionate (SAND), sulfosuccinimidyl (4-azidophenyl-dithio)-propionate (sulfoSADP) and 2-iminothiolane.HCl (Traut's reagent), are believed to provide similar results when conjugated with antibodies in accordance with the present invention, as illustrated herein by conjugation of antibodies with SPDP.

It is thought that the enhanced accumulation of the modified antibodies is due to amplified specific binding capacity. We have found that by conjugating, on average, only one PDP group per antibody molecule that a dramatic increase in the specificity of the molecule for its target cells occurs relative to unmodified antibody.

We have also discovered that modification of IgG by the conjugation of one or more PDP groups, advantageously, also enhances clearance from normal tissues. Although not wishing to be bound by any particular explanation of this effect, we believe that this is because modification with SPDP leads to fragmentation of the antibody to a form which has a molecular weight below the threshold for glomerular filtration, thus allowing for rapid elimination of the fragments. It is possible that fragmentation of the antibody to the monovalent form of the antibody occurs. Whatever the exact form of the resulting fragments, the elimination of these fragments is, advantageously, not so rapid so as to curtail the diagnostic or therapeutic effectiveness of the modified antibodies.

The modified antibodies of the present invention, advantageously, have surprisingly enhanced diagnostic and therapeutic effectiveness relative to fragments of antibodies, such as F(ab') or F(ab')$_2$.

The following example shows an exemplary method for the introduction of, on average, one PDP group to a monoclonal antibody.

EXAMPLE 1

Modification of Lym-1 with SPDP

Lym-1 (IgG$_{2a}$), the monoclonal antibody against B cell lymphoma was obtained as in Epstein, A.L. et al., Two New Monoclonal antibodies, Lym-1 and Lym-2, Reactive with Human B-lymphocytes and Derived Tumors, with Immunodiagnostic and Immunoreactive Potential, *Cancer Res.* 47: 830-840 (1987), the disclosure of which is hereby incorporated by reference. The Lym-1 MAb's were functionalized using SPDP, a heterobifunctional reagent which reacts with free amino groups on antibodies as in Carlson, J. et al., Protein Thiolation and Reversible Protein-Protein Conjugation: N-succinimidyl 3-(2-pyridyldithio)propionate, A New Heterobifunctional Reagent, *Biochem. J.* 173: 723-737 (1978), the disclosure of which is hereby incorporated by reference. To a 5 mL test tube containing 1 mL of Lym-1 (10 mg/mL) in PBS, pH 7.2, was added 20 μL of 3 mg SPDP in 1 mL ethanol and 40 μL, N,N-dimethylformamide. This mixture was incubated for 15 minutes at room temperature with continuous mixing using an orbital shaker apparatus set at normal speed. After incubation, the functionalized Lym-1 solution was purified by passage through a PD-10 column equilibrated with PBS.

The degree of functionalization of Lym-1 with SPDP was determined to be an average of one PDP group per molecule by measurement of release of pyridine-2-thione at 343 nm after reduction of an aliquot of the Lym-1 solution with molar excess of 7 mg dithioerythritol in phosphate buffer saline solution (PBS), pH 7.2., as in Grassetti, D.R. and Murray, J.F., Determination of Sulfhydryl Groups with 2,2'-or 4,4'-dithiodipyridine, *Arch. Biochem. Biophys.* 119: 41-49 (1967), the disclosure of which is hereby incorporated by reference.

The modified antibody from Example 1 was analyzed by Fast Protein Liquid Chromatography (FPLC) in order to show that the antibodies remained substantially intact. This analysis is shown in Example 2.

EXAMPLE 2

Analysis of Modified Lym-1 through Fast protein Liquid Chromatography (FPLC)

Analysis of modified antibody, from Example 1, was achieved by Fast protein Liquid Chromatography (FPLC) equipped with a fixed wavelength UV spectrophotometer set at 280 nm. Size exclusion chromatography was performed on a superose-12 column (Pharmacia) with PBS pH 7.2 as the solvent system, eluting at flow rate of 1 mL/min. The modified Lym-1 appeared at a retention time of 690 seconds, identical to the retention time of unlabeled intact Lym-1.

Thus, Example 2 shows that the SPDP-modified antibodies behaved virtually identically to the unmodified antibodies in FPLC. This data shows that the modification likely did not lead to breakdown of the intact molecules in vitro.

In order to further study the modified MAb's for in vivo testing, radiolabelling of the modified MAb's was performed. The radiolabelling is shown in Example 3.

EXAMPLE 3

Direct Radioiodination of Modified Lym-1

One batch of PDP modified Lym-1 and intact Lym-1 were iodinated with $^{125}$I, and another batch labeled with $^{131}$I using the modified chloramine T method of Mills, S.L. et al., $^{123}$I Radiolabelling of Monoclonal antibodies for In Vivo Procedures, *Hybridoma* 5: 265-275 (1986), the disclosure of which is hereby incorporated by reference. Briefly, to a 5 mL test tube containing 100 μg monoclonal antibody in 100 μL PBS, was added the appropriate iodine isotope, $^{125}$I or $^{131}$I depending on the batch, and 10 μL of 43 mM aqueous solution of chloramine T. The reaction was quenched after 3 minutes with 20 μL of 120 mM solution of sodium metabisulfite. The radiolabeled antibodies were purified using a Sephadex G-25 column. This column consisted of a serological plastic pipette (8mm×200mm) plugged at the end with cotton ($V_O$=4.5 mL, $V_t$=12 mL). Each reaction mixture was loaded on a column and eluted with PBS, pH 7.2. Individual tubes containing 1-mL aliquots were counted, and the radiolabeled antibodies were recovered in tube 6 in 85-90% yield. These radiolabeled antibodies were stored in the refrigerator and administered to mice within 4 hours of labeling.

The radiolabeled MAb's from Example 3 were subjected to Instant Thin Layer Chromatography (ITLC) in order to determine the purity of the labeled MAb's This analysis is shown in Example 4.

EXAMPLE 4

Analysis of Radiolabeled Modified Lym-1 through Instant Thin Chromatography (ITLC)

Modified Lym-1 radiolabeled with $^{131}$I and modified Lym-1 radiolabeled with $^{125}$I via the chloramine T method of Example 3 were analyzed using an analytical ITLC system consisting of silica gel impregnated glass fiber. Strips (2×20 cm) were activated by heating at 110½° C. for 15 minutes prior to use; spotted with 1 μL of sample; air-dried and eluted with MeOH/H$_2$O (80:20) for approximately 12 cm; again air-dried, cut in half and counted, to determine protein-bound and non-protein-bound radioactivity. Both forms of radiolabeled Lym-1 antibodies had an $R_f$ value of 0 and showed radiochemical purity of $\geq$ 99%. Analysis of intact Lym-1 labeled in the same way as in Example 3 revealed the same purity.

Thus, Example 4 shows that high purity radiolabeled antibodies could be obtained. The immunoreactivities of these radiolabeled MAb's were tested by their ability to bind to Raji cells. This analysis is shown in Example 5.

EXAMPLE 5

Analysis of Radiolabeled Modified Lym-1 through Immunoreactivity Assessment

The in vitro immunoreactivities of the radiolabeled modified Lym-1 and intact Lym-1 were evaluated by conventional live assay of $10^6$ Raji cells/tube by the method of Epstein, A.L. et al., supra. Briefly, Raji cells resuspended in 100µL of 1% bovine serum albumin in PBS was pipetted into a triplicate set of test tubes. One hundred µL of the labeled Lym-1 was added to each test tube (100,100 cpm/tube) and incubated for 30 minutes at room temperature with continuous mixing using an orbital shaker. After incubation, the cells were washed three times with 1% bovine serum in PBS by spinning the tubes at 1000 rpm for 5 minutes, decanting the supernatant and resuspending the cells in 200 µL PBS. Following completion of the washes, bound Lym-1 was detected by measuring the radioactivity bound to the cells using a gamma counter. The results showed that the binding activity of the modified Lym-1 was 87%, whereas the intact Lym-1, which served as a standard control, had a binding activity of 80%.

Thus, Example 5 shows that the modified Lym-1 was more immunoreactive in vitro than the unmodified Lym-1. In order to gain a preliminary assessment of the stability of the activity of the modified antibodies in vivo, modified MAb's were analyzed for their stability in serum, as shown in Example 6.

EXAMPLE 6

Analysis of Radiolabeled Modified Lym-1 through Serum Stability

Monoclonal antibodies of modified Lym-1 and intact Lym-1 which was labeled directly with I-125 were added to each of several triplicate sets of fresh mouse serum to a final concentration of 100 µg/mL. The tubes were incubated at 37½° C. in a humidified incubator maintained in 5% $CO_2$ in air. At times between 0 and 8 days, protein-bound activity was determined by adding 900 µL of 100% trichloroacetic acid (TCA) to 100 µL aliquots. After a five-minute incubation at room temperature, protein precipitates were sedimented by centrifugation, and 500 µL of supernatant were withdrawn from each tube and counted for radioactivity in a gamma counter. Data were expressed as the mean percentage counts precipitated minus that of the control tubes. The results showed that at each time point after incubation, modified $^{125}$I-Lym-1 was as stable as the $^{125}$I labeled intact Lym-1 which served as a standard control. The results further showed that >92% of activity present in the modified Lym-1 following an 8-day incubation at 37½° C. was TCA precipitable.

Thus, Example 6 showed that the stability of the activity of the modified antibodies was maintained in serum for at least 8 days. In order to evaluate whether the modified MAb's remained intact after incubation in serum, HPLC analysis of the modified Lym-1 after incubation was performed, as shown in Example 7.

EXAMPLE 7

Analysis of Modified Lym-1 by HPLC

HPLC analyses were performed on a Waters system equipped with size exclusion columns (SW 300) with 0.1M neutral phosphate buffer as eluting solvent and a flow rate of 1 ml/min. The eluate was detected with a radioisotope detector. The labeled modified Lym-1 product mixture from Example 6 revealed one major peak of a low molecular weight species with an elution time of 750 seconds, plus a small quantity at 690 seconds. The intact Lym-1 gave a single peak with a retention time of 690 seconds.

Thus, Example 7 shows that the serum incubated modified Lym-1 samples had an apparent molecular weight in HPLC analysis lower than that of intact Lym-1. In contrast, Example 2 showed that unincubated modified Lym-1 had an identical retention time to intact Lym-1. Thus, the modified Lym-1 showed an apparent loss of molecular weight in FPLC analysis upon incubation in serum.

To further verify the apparent loss of molecular weight of the modified Lym-1 upon incubation in serum, polyacrylamide gel electrophoresis of the samples was performed, as shown in Example 8.

EXAMPLE 8

Analysis of Radiolabeled Modified Lym-1 through SDS-Polyacrylamide Gel Electrophoresis (SDS-PAGE)

The same aliquots of each incubated serum mixture from Example 6 were serially checked by non-reduced SDS-PAGE. For this study, samples were run on 10% acrylamide gels, dried carefully and exposed in the usual way to a photographic film as in Laemmli, U.K., Cleavage of Structural Proteins During the Assembly of the Head of Bacteriophage T4, Nature 227: 680–685 (1970), the disclosure of which is hereby incorporated by reference. This analysis revealed that intact $^{125}$I-Lym-1 was evident at $M_r$ 200,000, whereas modified $^{125}$I-Lym-1 was observed at a distinct band corresponding to a smaller molecular weight at approximately $M_r$ 116,000. Thus, the present example shows that incubation of the modified antibodies in serum results in modified apparent molecular weight on acrylamide gels, verifying the results of HPLC analysis.

EXAMPLE 9

Test for Deiodination of Labeled Lym-1 in Serum

The same samples from Example 6 were also examined over an 8-day study to see if there had been any loss of radioactivity from the radiolabeled Lym-1; such loss can be interpreted as evidence of deiodination in serum. The data showed virtually no loss of radioactivity over this period, confirming that a very stable attachment of iodine had been obtained in these immunoconjugates.

Thus, Examples 7–9 show that the modified antibodies while retaining virtually full activity after incubation in serum, appeared to break down into molecules of apparent molecular weight of 116,000. As stated above, it is possible that this loss of molecular weight is due to the breakdown of the antibodies into their monovalent form. In any event, it is believed that the loss in apparent molecular weight is due to the breakdown of the modified antibodies into fragments thereof.

After discovering the foregoing unexpected change in apparent molecular weight of the modified antibodies when incubated in serum, we tested the stability of the modified MAb's in vivo. We performed these in vivo tests in order to determine total body clearance time. An example of these tests is shown in Example 10.

EXAMPLE 10

Total Body Clearance

Experiments were performed in which three groups of athymic nude mice (n=5) were given intraperitoneal injections of (a) intact antibody, (b) F(ab')$_2$ fragments, or (c) modified antibody of Lym-1 labeled with I-131 using the chloramine T method. The whole-body activity at injection and serially thereafter was measured with a dosimeter. This study demonstrated that the total body clearance of radioactivity varied with the antibody preparation. Results are shown in FIG. 2.

Figure 2:
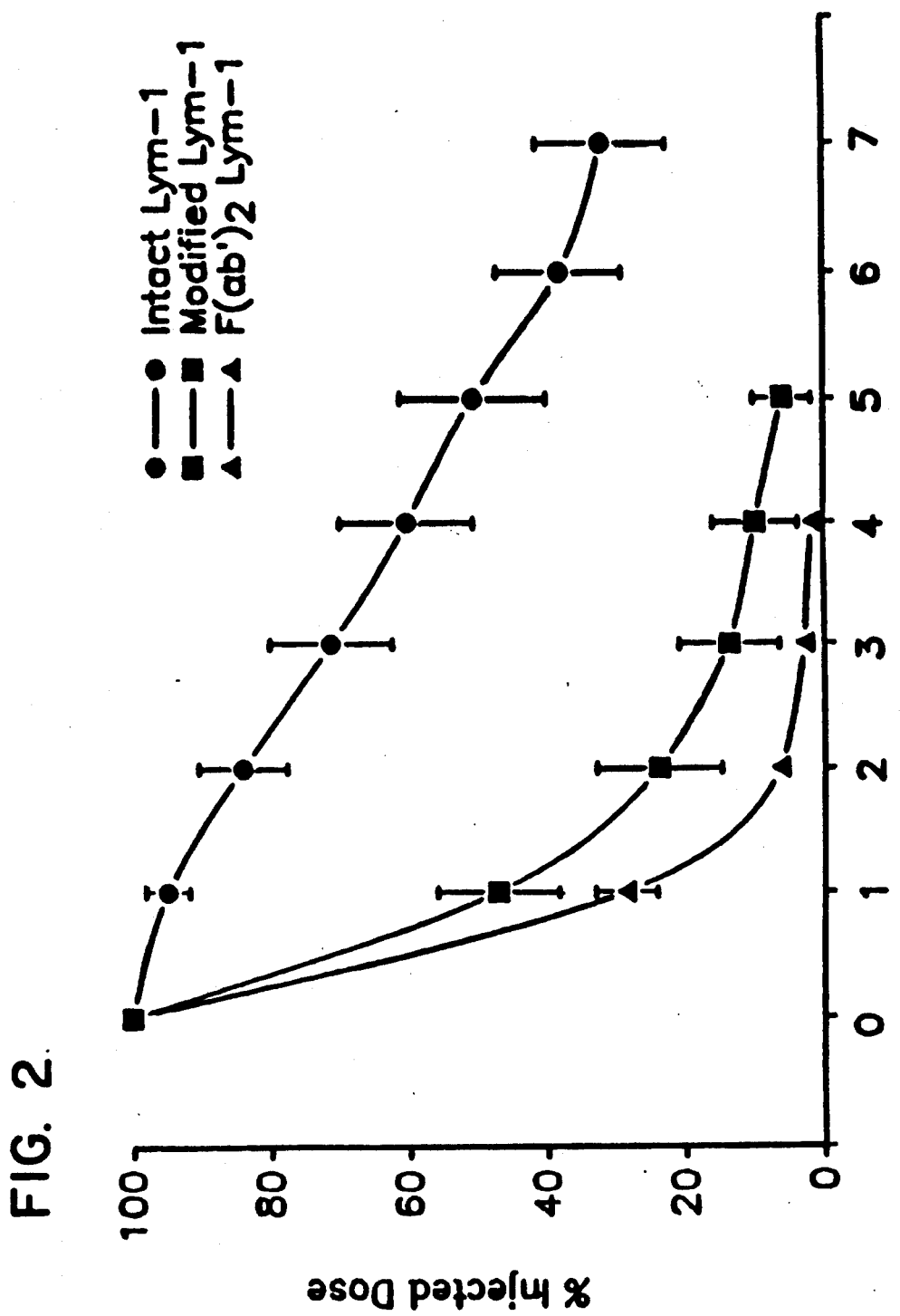
FIG. 2 shows whole body retention of different preparations of radio-labeled MAb's Lym-1 in athymic nude mice.

FIG. 2 shows that the modified Lym-1 cleared from the whole body faster, with a biological half-life (t$\frac{1}{2}$) of 20 hours, than the intact Lym-1 (t$\frac{1}{2}$=5 days). The clearance of F(ab')$_2$ fragments was, however, two times faster, with a biological half-life of 10 hours, than the modified Lym-1. The data showed that modified Lym-1 is cleared at a rate intermediate between the rapidly-cleared F(ab')$_2$ fragments and the slowly-cleared intact antibody.

Thus, it can be seen from the data from Example 10 that the modified antibodies are cleared from the body more rapidly than the relatively highly persistent intact antibodies, yet not so rapidly as F(ab')$_2$ fragments.

An ideal agent for immunotherapy would persist in the bloodstream for long enough periods to produce the desired toxic effect, yet not so long to cause unintended toxic side effects. The data from Example 10 suggested that the modified antibodies exhibited potentially ideal persistence times when used in immunotherapy.

As discussed above, an agent for immunotherapy would also be highly specific towards its target cells. Thus, we tested the specificity of the modified MAb's relative to both intact MAb's and the F(ab')$_2$ fragments in the following examples. Example 11 shows the methods used in all of the subsequent biodistribution studies.

EXAMPLE 11

Biodistribution Studies

Two groups of six-week-old nude mice were injected with Raji cells (10$^7$) subcutaneously in the thigh region. The tumors were grown for three weeks until they became larger than 1 cm in diameter. Paired-label studies, as described below, were performed using each group of mice. In the first group (n=6), each mouse was injected i.p. with a 0.2 mL inoculum containing 10 μg of modified Lym-1 labeled with I-131 at 12 μCi/μg (120μCi/mouse), and 10 μg of intact Lym-1 labeled with I-125 at 2.5μCi/μg (25μCi/mouse). In the second group (n=4), mice received a 0.2 mL inoculum containing 10 μg of modified Lym-1 labeled with I-131 at 12 μCi/μg (120μCi/mouse), and 10 μg of F(ab')$_2$ fragments labeled with I-125 at 2.5μCi/μg (25μCi/mouse). In all experiments, mice were sacrificed by cervical dislocation at preselected times, post-injection, and various organs, blood and tumor were removed and weighed on an analytical balance. The samples were then counted in a gamma counter to determine the $^{131}$I and $^{125}$I activity. $^{125}$I counts were adjusted for crossover from the $^{131}$I channel by subtracting 17% of $^{131}$I channel counts, a formula that was determined experimentally using a 1282 Compugamma gamma counter (LKB). The data were also corrected for the radiation decay of the $^{131}$I isotope according to the days on which the animals were sacrificed. For each mouse, data was expressed as cpm per gram tumor/cpm per gram organ, % dose/gram, and % dose/organ From these data, the mean and standard deviation were calculated for each group.

Example 12 compares the biodistribution of the modified MAb's to intact MAb's using the methods of Example 11.

EXAMPLE 12

Biodistribution Study of Modified Lym-1 vs. Intact Lym-1

For this study, the intact Lym-1 antibody was compared to the modified Lym-1 antibody in the methods of Example 11. Intact Lym-1 produced a blood activity of 0.64% ID/g at 7 days after injection, as reported in Table I. At the end of the same time interval, the tumor had an activity of 3.92% ID/g.

As reported in Table I, Compared to the intact Lym-1, the modified Lym-1 cleared from blood faster and produced a blood activity of 0.14% ID/g at 7 days. At the end of the same time interval, the tumor produced 7.7%, which tended to be significantly higher than the corresponding activities of the intact Lym-1.

Figure 3:
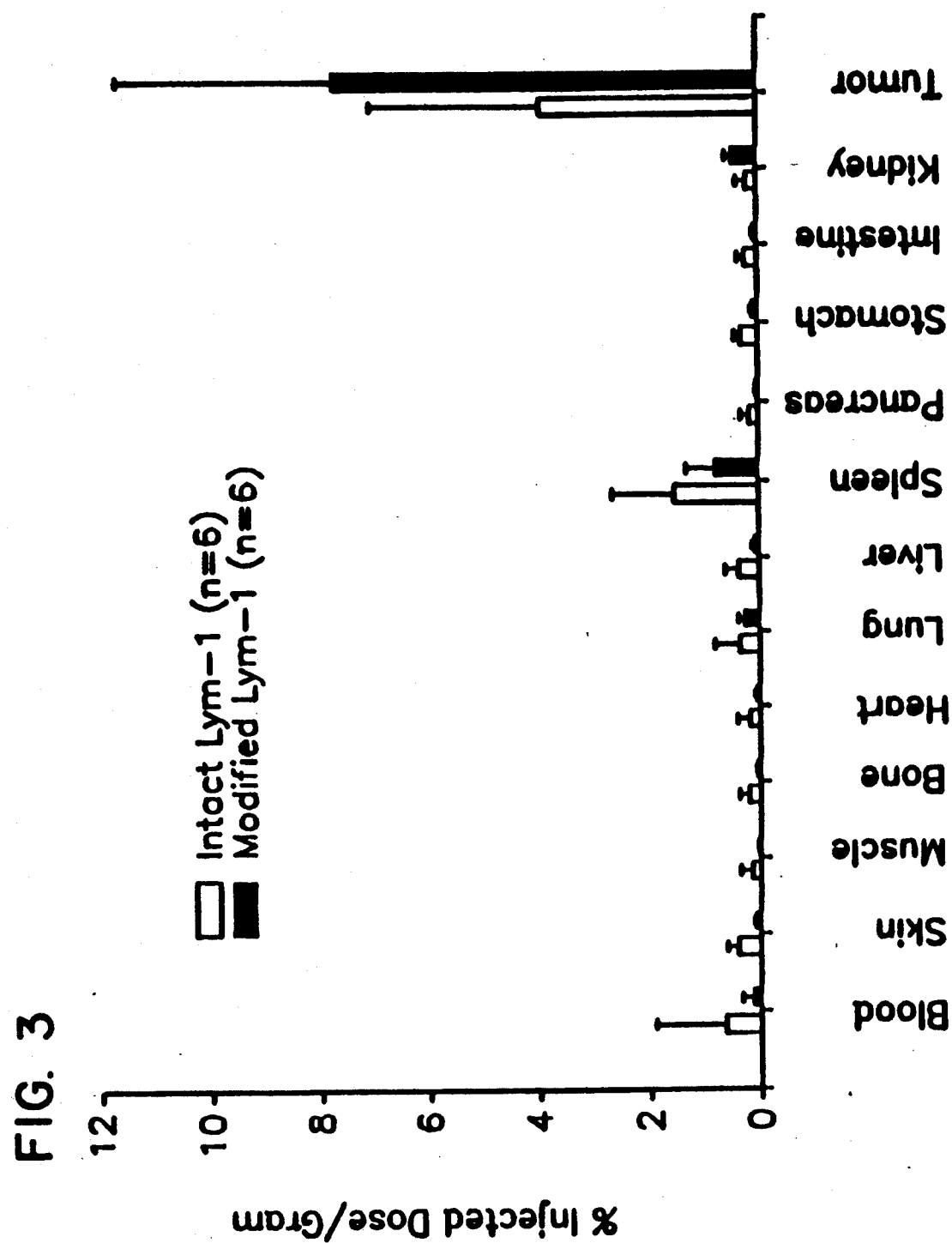
FIG. 3 shows the biodistribution as % of injected dose/gram of MAb's Lym-1 and modified Lym-1 in human lymphoma-bearing nude mice seven days after injection.
Figure 4:
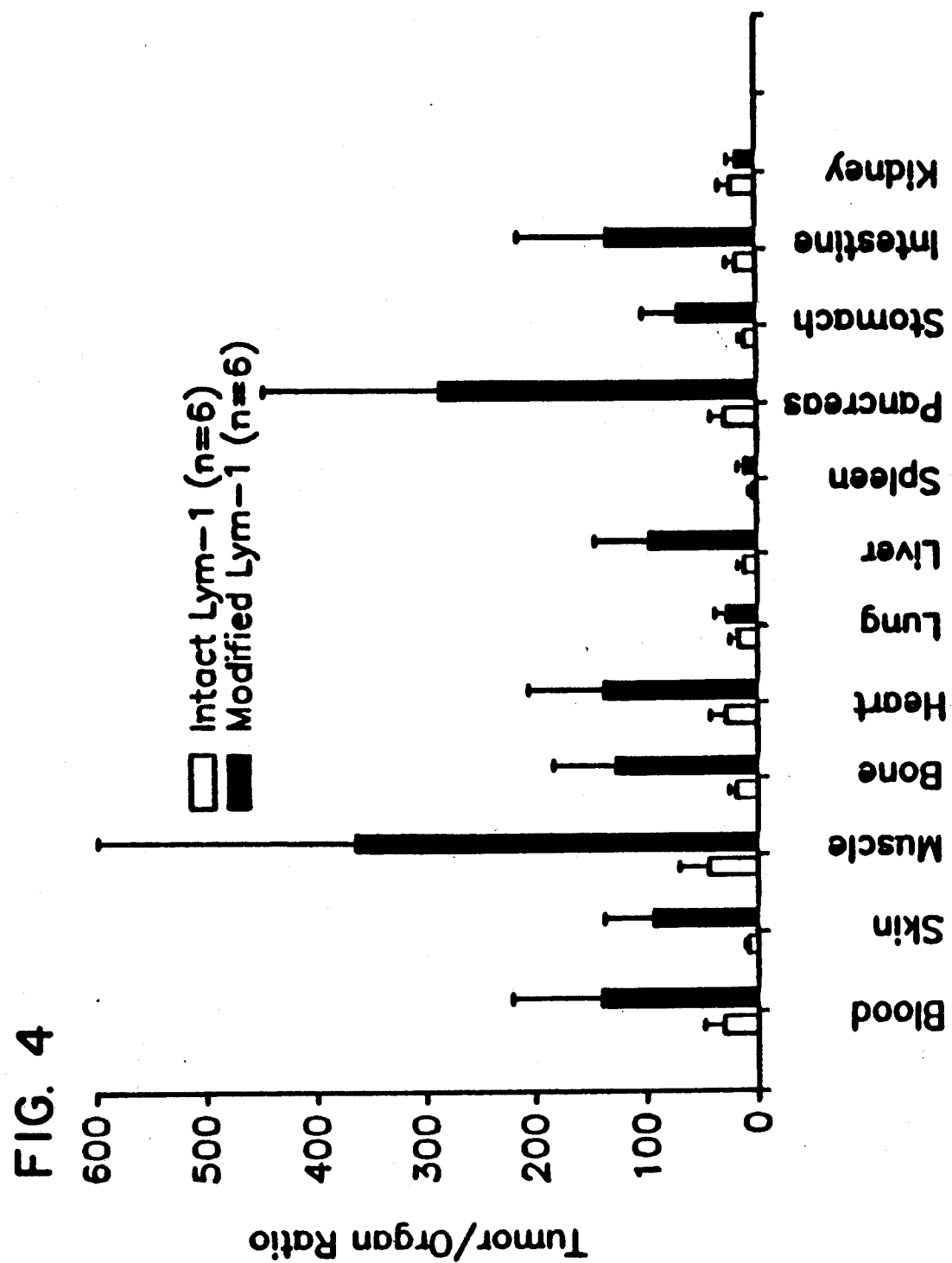
FIG. 4 shows the biodistribution as tumor/organ ratios of MAb's Lym-1 and Modified Lym-1 in human lymphoma-bearing nude mice seven days after injection.

Results of antibody reactivity from Example 12 in several organs are reported in Table I and shown graphically in FIG. 3 (%dose/gram) and FIG. 4 (tumor/organ).

TABLE I

BIODISTRIBUTION OF MODIFIED AND INTACT MONOCLONAL ANTIBODY LYM-1 IN RAJI TUMOR-BEARING NUDE MICE (N = 6) 7 DAYS AFTER INJECTION

| Organ | cpm/g tumor cpm/g organ | % dose/g | % dose/organ |
|---|---|---|---|
| Modified Lym-1 | | | |
| Blood | 140.07 (81.30)* | 0.14 (0.20) | — |
| Skin | 93.98 (43.40) | 0.09 (0.04) | — |
| Muscle | 364.53 (232.97) | 0.03 (0.03) | — |
| Bone | 126.96 (55.86) | 0.06 (0.02) | — |
| Heart | 137.34 (67.96) | 0.07 (0.04) | 0.01 (0.00) |
| Lung | 28.31 (10.34) | 0.28 (0.10) | 0.06 (0.02) |
| Liver | 96.80 (49.03) | 0.09 (0.05) | 0.15 (0.08) |
| Spleen | 12.02 (5.62) | 0.79 (0.53) | 0.03 (0.01) |
| Pancreas | 286.43 (159.92) | 0.04 (0.02) | 0.00 (0.00) |
| Stomach | 71.21 (30.72) | 0.11 (0.03) | 0.02 (0.01) |
| Intestine | 133.31 (80.82) | 0.07 (0.04) | — |
| Kidney | 17.63 (7.63) | 0.45 (0.12) | 0.14 (0.03) |
| Tumor | | 7.70 (3.95) | 2.98 (1.71) |
| Intact Lym-1 (Control) | | | |
| Blood | 30.72 (17.74) | 0.64 (1.26) | — |
| Skin | 8.83 (3.05) | 0.41 (0.20) | — |
| Muscle | 44.39 (26.16) | 0.15 (0.21) | — |
| Bone | 19.49 (6.08) | 0.21 (0.18) | — |
| Heart | 28.79 (13.76) | 0.19 (0.22) | 0.02 (0.02) |
| Lung | 16.98 (8.22) | 0.36 (0.46) | 0.07 (0.01) |
| Liver | 11.84 (5.95) | 0.37 (0.25) | 0.59 (0.46) |
| Spleen | 3.93 (3.74) | 1.52 (1.14) | 0.06 (0.03) |
| Pancreas | 29.35 (12.88) | 0.16 (0.17) | 0.02 (0.02) |
| Stomach | 11.00 (4.55) | 0.32 (0.11) | 0.07 (0.03) |
| Intestine | 18.06 (8.79) | 0.23 (0.13) | — |
| Kidney | 22.44 (10.61) | 0.20 (0.17) | 0.06 (0.05) |
| Tumor | — | 3.92 (3.11) | 1.02 (0.27) |

*Mean (standard deviation).

It can be seen from FIG. 3 that the modified antibodies produced a higher signal in the tumor than the intact antibodies. Additionally, the modified antibodies reacted less strongly than the intact MAb's for every organ tested, except for the kidney. It is not unexpected that a higher signal would be found in the kidney, because the antibodies are expected to be cleared through this organ. Due to the more rapid clearance rate of the modified MAb's relative to intact MAb's found in Example 10, a higher amount of modified MAb's in the kidney would be expected.

Referring to FIG. 4, showing the same data as FIG. 3 in a different form, it can be seen that the modified MAb's produced a significantly higher tumor/organ ratio than intact MAb's in every organ tested, except for kidney. Thus, it would be expected that the modified antibodies would produce a significantly lower background when used in immunoscintography. Moreover, it would also be expected that the modified antibodies would be more effective when used in immunotherapies due both to its higher affinity for tumor and lower affinity for non-target tissues. When used in immunotherapies, the modified antibodies would, thus, be expected to be more highly toxic to tumors and less toxic to non-target tissues. The immunotherapeutic use of the modified antibodies of the present invention is hereinafter explained in further detail.

We next compared the biodistribution of the modified MAb's with F(ab')$_2$ fragments of the otherwise unmodified antibody. Example 13 is illustrative of these experiments.

EXAMPLE 13

Biodistribution Study of Modified Lym-1 vs. F(ab')$_2$ Fragments of Lym-1

For this study, the F(ab')$_2$ fragments were compared with the modified Lym-1 MAb's Experiments were performed as in Example 11. Results are reported in Table II and shown graphically in FIGS. 4 and 5.

TABLE II

BIODISTRIBUTION OF MODIFIED AND INTACT MONOCLONAL ANTIBODY LYM-1 IN RAJI TUMOR-BEARING NUDE MICE (N = 4) 5 DAYS AFTER INJECTION

| Organ | cpm/g tumor cpm/g organ | % dose/g | % dose/organ |
|---|---|---|---|
| Modified Lym-1 | | | |
| Blood | 39.59 (14.84)* | 0.09 (0.03) | — |
| Skin | 13.69 (3.15) | 0.24 (0.06) | — |
| Muscle | 75.32 (16.22) | 0.04 (0.01) | — |
| Bone | 26.79 (7.18) | 0.12 (0.04) | — |
| Heart | 44.42 (11.34) | 0.08 (0.04) | 0.01 (0.01) |
| Lung | 15.78 (3.88) | 0.21 (0.07) | 0.04 (0.01) |
| Liver | 12.19 (4.25) | 0.29 (0.12) | 0.27 (0.10) |
| Spleen | 2.68 (1.01) | 1.34 (0.55) | 0.07 (0.03) |
| Pancreas | 42.17 (11.23) | 0.08 (0.03) | 0.01 (0.00) |
| Stomach | 14.16 (4.43) | 0.24 (0.07) | 0.05 (0.02) |
| Intestine | 28.36 (9.96) | 0.12 (0.05) | — |
| Kidney | 12.53 (3.15) | 0.27 (0.09) | 0.09 (0.03) |
| Tumor | — | 3.18 (0.89) | 3.16 (1.09) |
| F(ab')$_2$ Fragments (Control) | | | |
| Blood | 29.27 (13.17) | 0.05 (0.02) | — |
| Skin | 10.54 (2.78) | 0.12 (0.02) | — |
| Muscle | 55.50 (14.49) | 0.02 (0.01) | — |
| Bone | 23.73 (7.89) | 0.06 (0.02) | — |
| Heart | 35.19 (11.01) | 0.04 (0.02) | 0.00 (0.00) |
| Lung | 12.57 (3.69) | 0.10 (0.03) | 0.02 (0.00) |
| Liver | 10.43 (4.20) | 0.13 (0.05) | 0.12 (0.04) |
| Spleen | 2.59 (1.03) | 0.54 (0.21) | 0.03 (0.01) |
| Pancreas | 31.55 (9.82) | 0.04 (0.02) | 0.00 (0.00) |
| Stomach | 8.08 (3.31) | 0.17 (0.06) | 0.03 (0.01) |
| Intestine | 22.27 (7.93) | 0.06 (0.02) | — |
| Kidney | 10.05 (2.71) | 0.13 (0.04) | 0.04 (0.01) |

TABLE II-continued

BIODISTRIBUTION OF MODIFIED AND INTACT MONOCLONAL ANTIBODY LYM-1 IN RAJI TUMOR-BEARING NUDE MICE (N = 4) 5 DAYS AFTER INJECTION

| Organ | cpm/g tumor cpm/g organ | % dose/g | % dose/organ |
|---|---|---|---|
| Tumor | — | 1.23 (0.24) | 1.42 (0.48) |

*Mean (standard deviation).

Figure 5:
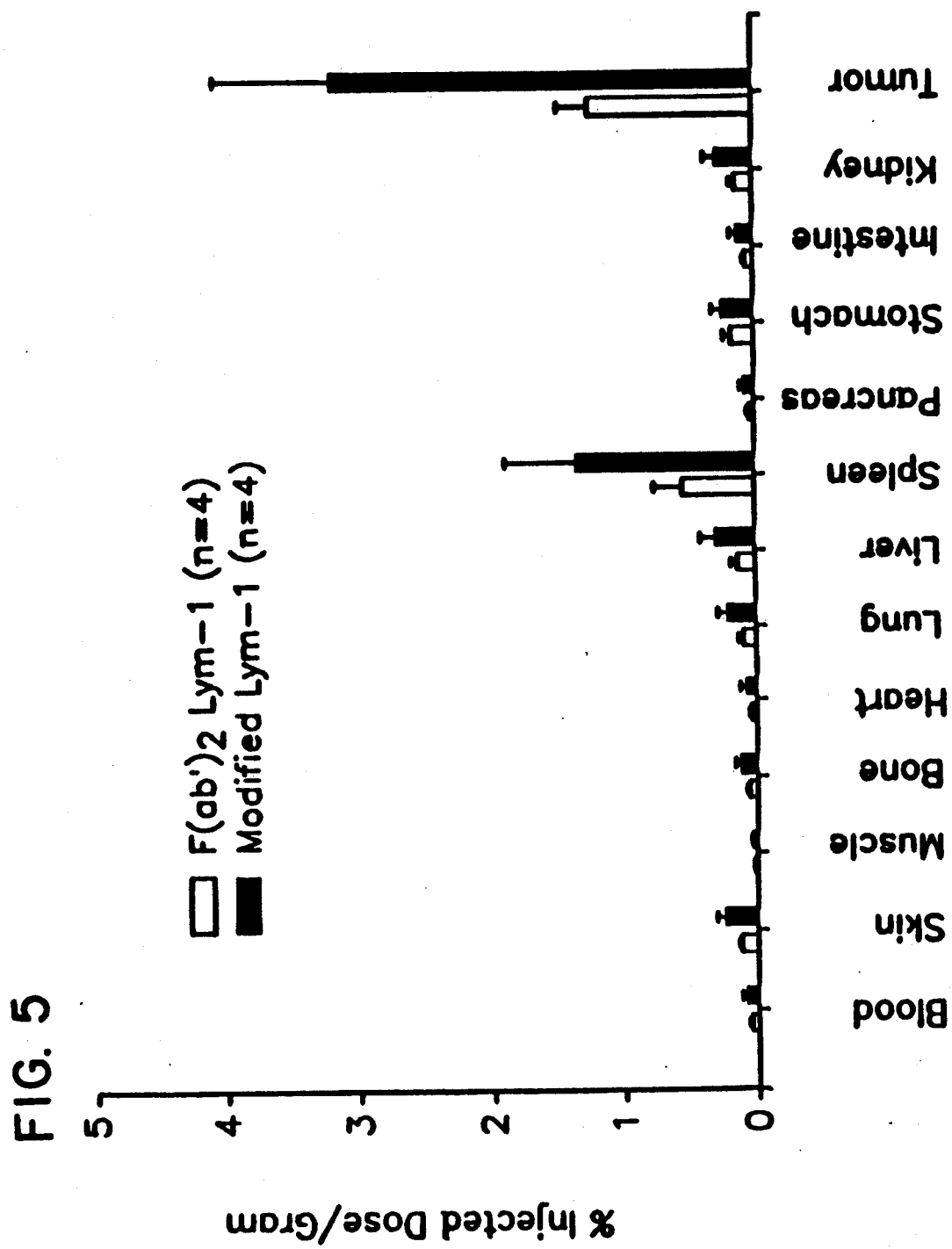
FIG. 5 shows the biodistribution as % of injected dose/gram of MAb's Lym-1 F(ab')2 and Modified Lym-1 in human lymphoma-bearing nude mice five days after injection.

Table II shows that the modified Lym-1 cleared more slowly from the blood than the F(ab')$_2$ fragments. The modified Lym-1 produced a blood activity of 0.09% ID/g higher than the fragments (0.05%) at 5 days post-injection. FIG. 5 shows that the tumor activity of the modified Lym-1 was about two-and-one-half times higher than the corresponding activity of the F(ab')$_2$ fragments. The activity of the modified Lym-1 was higher than the F(ab')$_2$ fragments for all of the various organs tested, including kidney. This is consistent with the theory that more rapidly cleared antibodies accumulate in the kidney.

Figure 6:
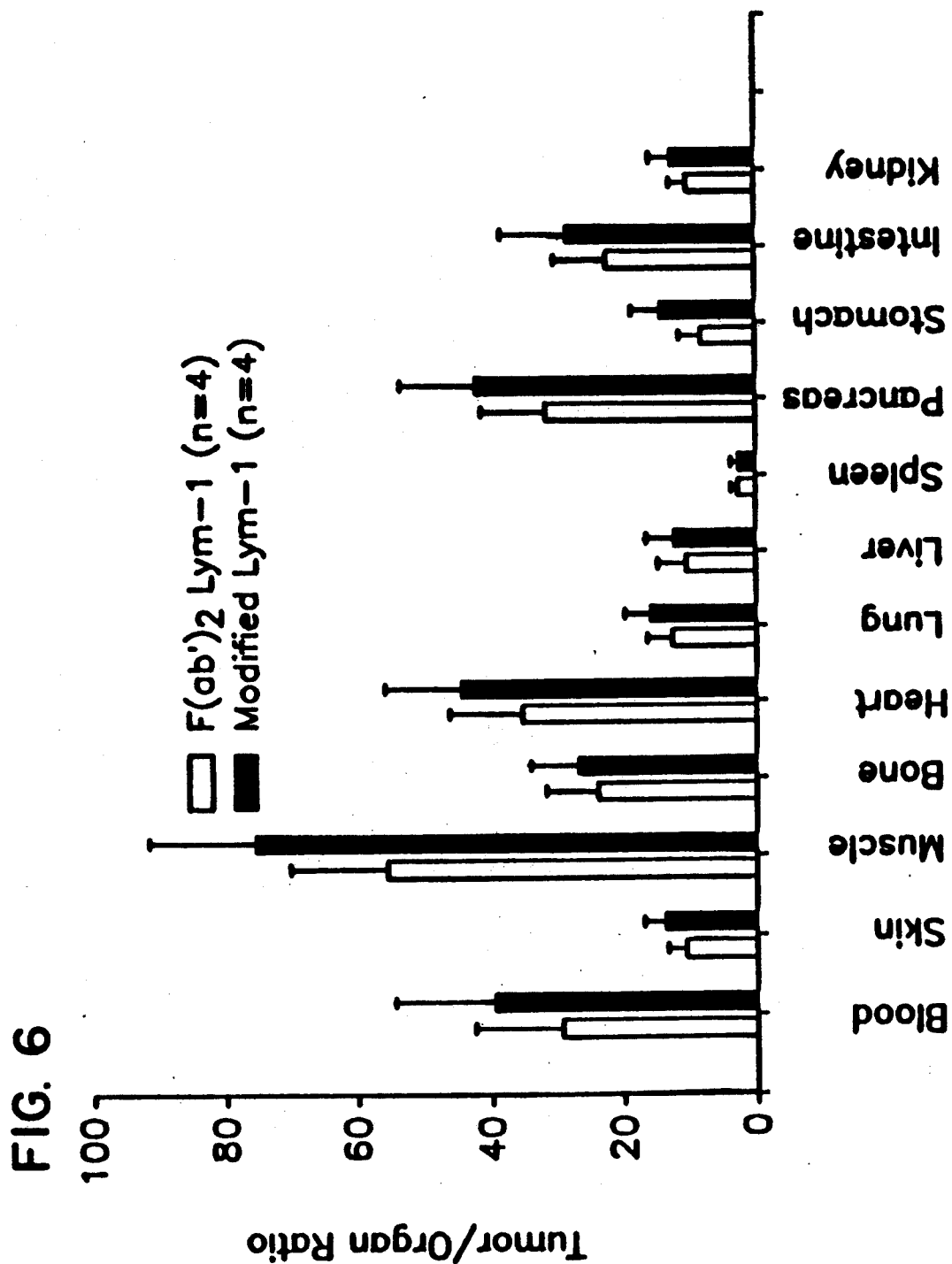
FIG. 6 shows the biodistribution as tumor/organ ratio of MAb's Lym-1 F(ab')2 and Modified Lym-1 in human lymphoma-bearing nude mice five days after injection.

Moreover, FIG. 6 shows that the tumor-to-organ ratios for modified Lym-1 are higher than those of the F(ab')$_2$ fragments for all of the organs tested. Thus, the experiments of Examples 12 and 13 confirm that the modified antibodies of the present invention have a higher activity for their target tumor than either intact MAb's or F(ab')$_2$ fragments. Additionally, the tumor-to-organ data of these experiments shows that the modified antibodies have higher specificity for tumor than either the intact MAb's or F(ab')$_2$ fragments.

Thus, we tested the ability of the modified MAb's of the present invention to produce improved immunoscintographic results. One example of these tests is shown in Example 14.

EXAMPLE 14

Imaging Studies of Lym-1

Figure 7:
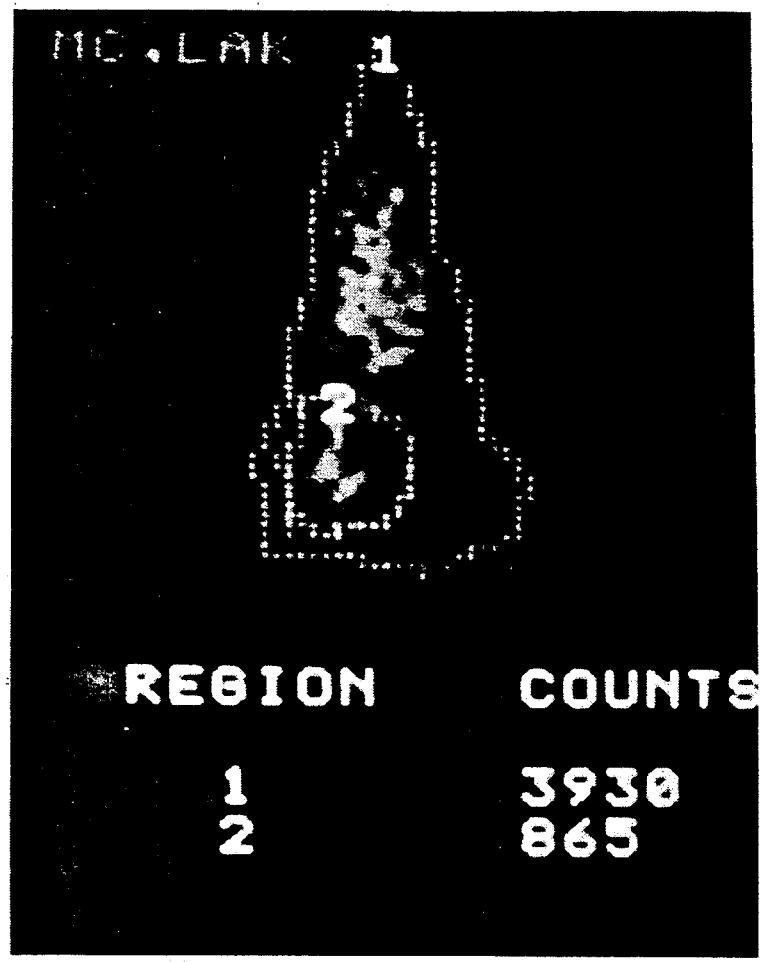
FIG. 7 shows the image obtained on day 7 after injection of I-131 labeled intact Lym-1.
Figure 8:
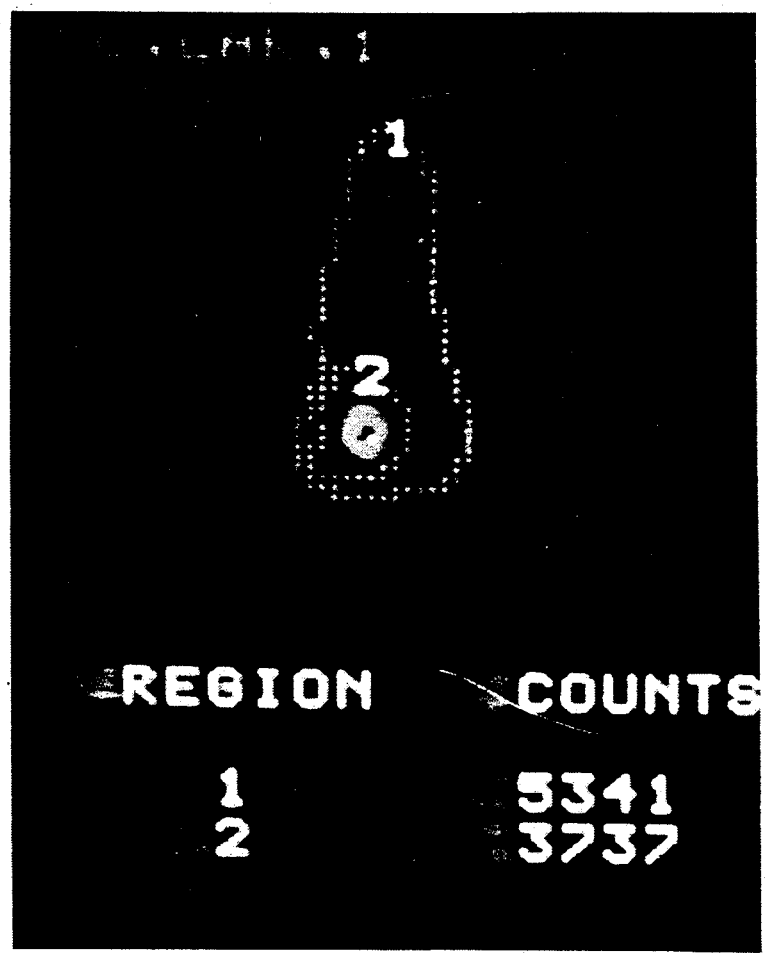
FIG. 8 shows the image obtained on day 7 after injection of I-131 labeled modified Lym-1.

Tumor-bearing nude mice were imaged using a pinhole collimator and a spectrum 91 gamma camera (Raytheon). Image analyses of these animals provided an estimate of tumor/whole body antibody distribution after injection. Seven days after injection, the mice were anesthetized with 2 mg Ketamine HCl and 0.4 mg Xylazine administered as a 0.2 mL s.c. inoculation. The immobilized mice where then imaged in a posterior position with the camera preset to record 10,000 counts. No background substraction was performed. Photographic images were obtained using Polaroid Type 330 Pack film. Two areas in each image were defined: (a) region 1, whole body; (b) region 2, tumor. FIGS. 6–8 show exemplary scintographs (also known as scintograms) produced by these experiments.

Immunoscintography imaging with intact Lym-1 was attempted at 7 days after injection and was not satisfactory, as seen in FIG. 6. FIG. 6 shows that although the tumor was visualized, the rest of the animal was also visualized. FIGS. 7 and 8 show the images of two different Raji tumor-bearing animals injected with labeled modified Lym-1 at the same time after injection. It can be seen that both FIGS. 7 and 8 show concentration of the labeled modified Lym-1 at the tumor at levels much higher than those at the tumor produced by the intact Lym-1, seen in FIG. 6. More importantly, the ratio of label at the tumor to the background of the whole mouse produced by the modified Lym-1 was several times higher than that of the intact Lym-1. Thus, FIGS.

7 and 8 show a clear definition of the tumor, with little or no background radioactivity.

Figure 9:
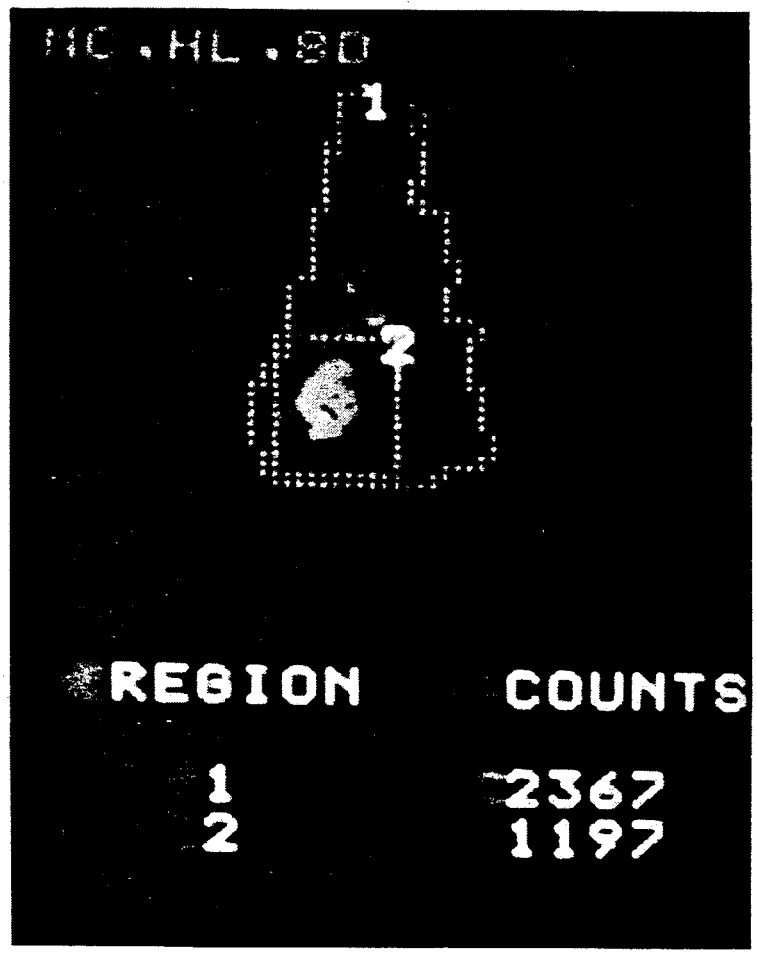
FIG. 9 shows the image obtained on day 7 after injection of I-131 labeled modified Lym-1.
Figure 10:
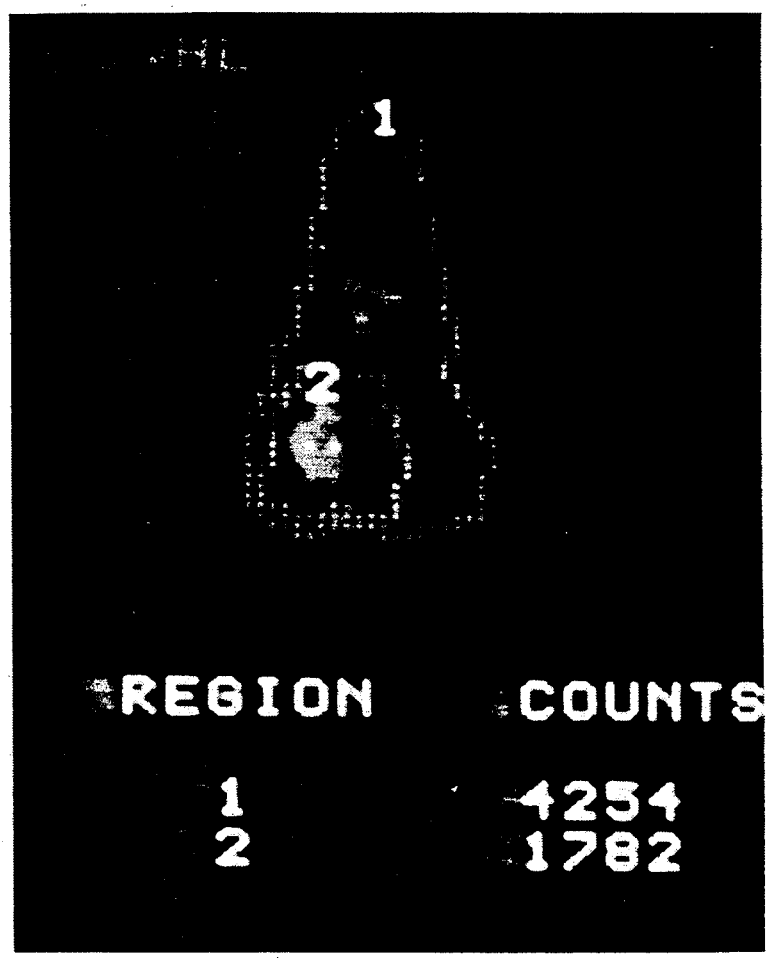
FIG. 10 shows t he image obtained on day 5 after injection of I-131 labeled modified Lym-1.

Moreover, a satisfactory visualization of the tumor could be obtained at 5 days after injection when using the modified Lym-1. FIG. 10 shows a 5-day image taken of the same animal as shown in FIG. 9 at 7 days. As can be seen, the 5-day image of FIG. 10 was significantly superior to the image produced by intact Lym-1 at 7 days (FIG. 7). Results were similar for all animals tested.

This study suggests that the use of modified antibody fragments exhibit greater specific activity to tumor antigens, allowing more absolute concentration of antibody to accumulate in tumor. This is confirmed by our results that showed that the absolute concentration of modified Lym-1 fragments is about 2 times the intact Lym-1 concentration 7 days after injection and about two and a half times the F(ab')₂ fragments at five days.

The much faster clearance of the modified Lym-1 fragments also significantly decreases the time required to reach high tumor to background ratios and thus results in better imaging in less time than intact antibody.

In order to demonstrate the general utility of the modification of the present invention in improving the specificity and activity of antibodies, we modified additional MAb's. Tests of these various modified MAb's are shown in Examples 15-18.

EXAMPLE 15

Clearance Rate of Monoclonal Antibody B72.3

B72.3 (IgG$_1$), the monoclonal antibody against colon carcinoma, was obtained as in Colcher, D. et al, A Spectrum of Monoclonal antibodies Reactive with Human Mammary Tumor Cells, *Proc. Natl. Acad. Sci.* 78:3199-3203 (1981), the disclosure of which is hereby incorporated by reference. B72.3 MAb's were functionalized with an average of one PDP group per molecule according to the method of Example 1.

Figure 11:
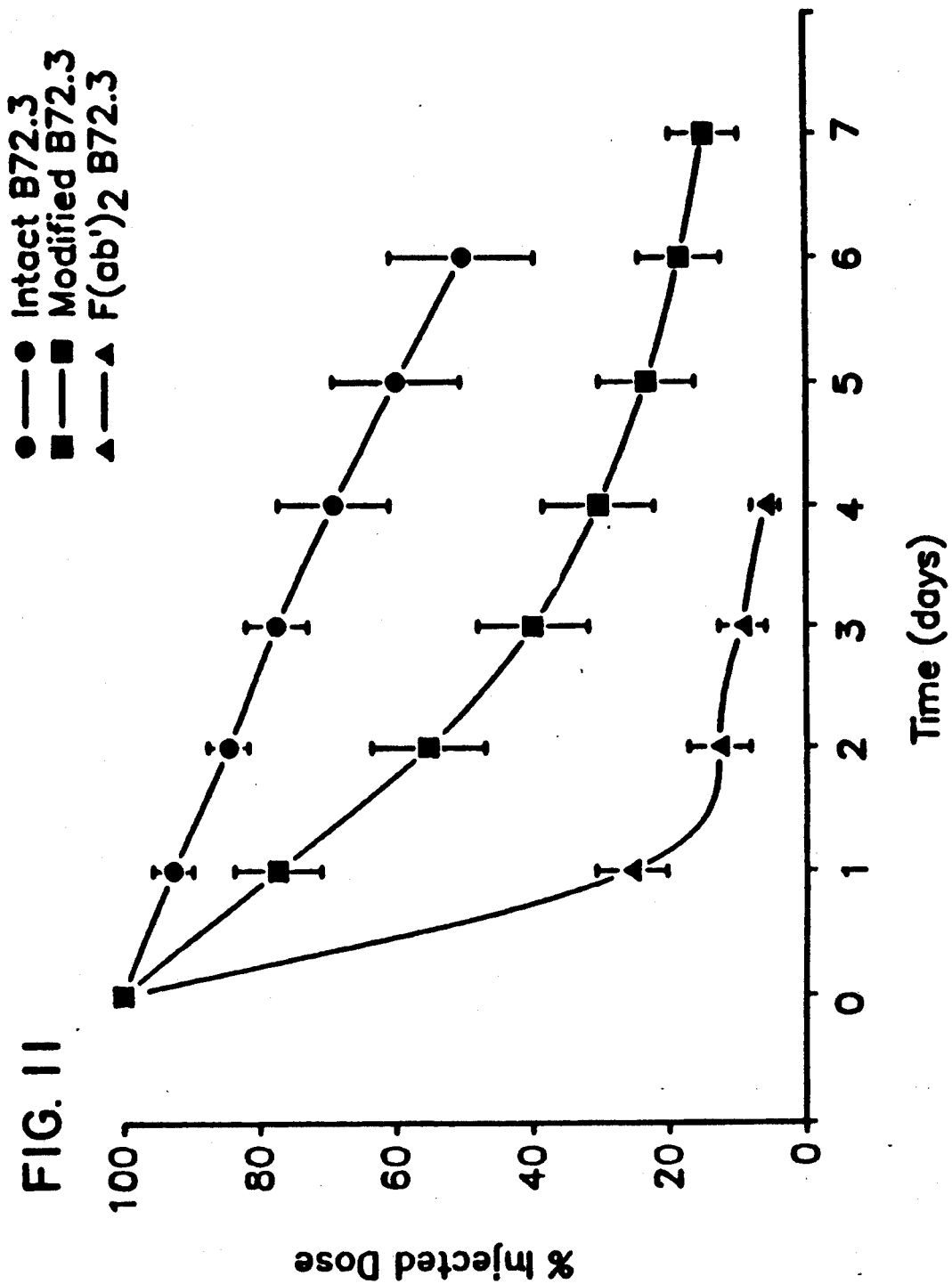
FIG. 11 shows the whole body retention of different preparations of radio-labeled monoclonal antibodies B72.3 in athymic nude mice.

The modified B72.3 MAb's were radiolabeled by the method of Example 3. Total body clearance times were measured as in Example 10. FIG. 11 shows the results of these total body clearance experiments. The modified antibodies showed a decrease in whole body half-time clearance from the approximately 6 days of intact MAb's to approximately 2.5 days for the modified antibodies. The half-time clearance of F(ab')₂ fragments was, as for the Lym-1 fragments, faster than the modified antibodies, with a half-time of approximately 12 hours. Thus, the results showed that modified B72.3 behaved similarly to the modified Lym-1 in having a half-time clearance intermediate between that of the F(ab')₂ fragments and intact antibody.

EXAMPLE 16

Biodistribution of B72.3

Figure 12:
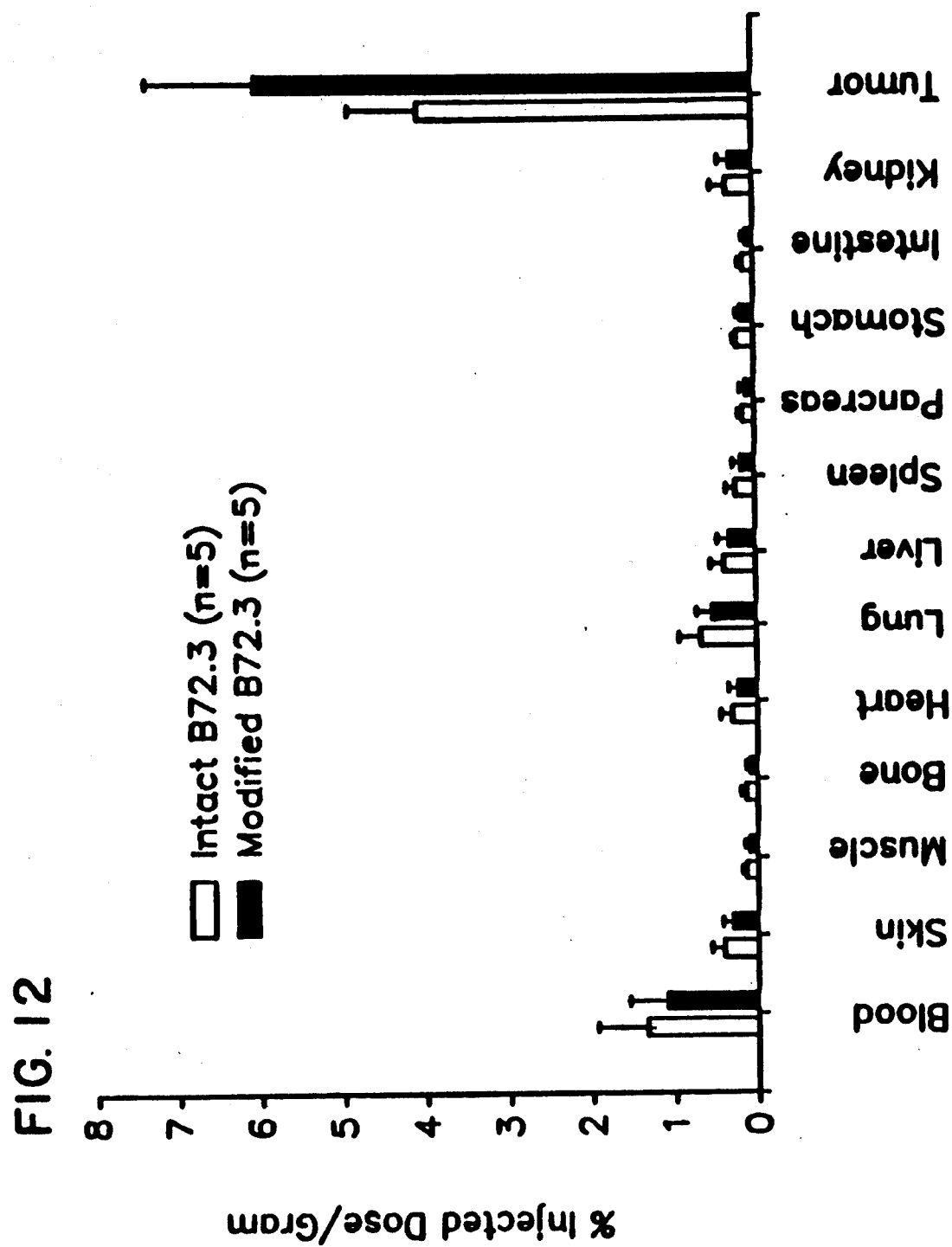
FIG. 12 shows the biodistribution as % of injected dose/gram of MAb's B72.3 and Modified B72.3 in LS174T colon carcinoma-bearing nude mice four days after injection.

Paired-label biodistribution studies for two groups of five mice each were performed in athymic nude mice bearing the human LS174T colon carcinoma. One group was injected with the intact I-125 labeled B72.3, while the other was injected with the modified I-131 labeled B72.3. The experiment also compared the biodistribution in tumor, blood and various organs. The methods employed were as in Examples 11-13. The data is reported in FIG. III, and shown graphically in FIGS. 11 and 12.

TABLE III

BIODISTRIBUTION OF MODIFIED AND INTACT MONOCLONAL ANTIBODY B72.3 IN THE HUMAN LS174T COLON CARCINOMA-BEARING NUDE MICE (N = 5) 4 DAYS AFTER INJECTION

| Organ | cpm/g tumor cpm/g organ | % dose/g | % dose/organ |
|---|---|---|---|
| Modified B72.3 | | | |
| Blood | 6.16 (2.32)* | 1.10 (0.45) | — |
| Skin | 20.81 (3.92) | 0.31 (0.12) | — |
| Muscle | 61.58 (16.16) | 0.11 (0.05) | — |
| Bone | 65.25 (15.04) | 0.10 (0.04) | — |
| Heart | 31.41 (18.44) | 0.24 (0.11) | 0.03 (0.02) |
| Lung | 11.89 (3.25) | 0.54 (0.18) | 0.14 (0.04) |
| Liver | 21.61 (10.36) | 0.33 (0.14) | 0.43 (0.17) |
| Spleen | 37.89 (15.00) | 0.18 (0.09) | 0.02 (0.01) |
| Pancreas | 60.23 (23.73) | 0.12 (0.06) | 0.02 (0.01) |
| Stomach | 37.74 (9.20) | 0.17 (0.05) | 0.04 (0.01) |
| Intestine | 68.31 (28.27) | 0.10 (0.04) | — |
| Kidney | 24.56 (10.07) | 0.29 (0.13) | 0.09 (0.04) |
| Tumor | — | 6.02 (1.33) | 6.45 (1.53) |
| Intact B72-3 (Control) | | | |
| Blood | 3.43 (1.13) | 1.34 (0.60) | — |
| Skin | 10.44 (1.80) | 0.41 (0.15) | — |
| Muscle | 31.78 (8.86) | 0.14 (0.05) | — |
| Bone | 33.36 (9.84) | 0.14 (0.06) | — |
| Heart | 16.57 (8.28) | 0.30 (0.14) | 0.04 (0.02) |
| Lung | 6.42 (1.59) | 0.68 (0.28) | 0.18 (0.08) |
| Liver | 11.85 (4.78) | 0.39 (0.16) | 0.52 (0.24) |
| Spleen | 18.94 (5.61) | 0.24 (0.12) | 0.02 (0.01) |
| Pancreas | 29.80 (9.42) | 0.15 (0.05) | 0.02 (0.01) |
| Stomach | 18.88 (3.83) | 0.22 (0.04) | 0.05 (0.01) |
| Intestine | 35.61 (13.48) | 0.13 (0.06) | — |
| Kidney | 15.20 (6.40) | 0.33 (0.18) | 0.11 (0.06) |
| Tumor | — | 4.04 (0.84) | 4.28 (0.78) |

*Mean (standard deviation).

As can be seen in Table III, intact B72.3 antibody produced a blood activity at 1.34% ID/g at 4 days after injection, and an activity of 4.04% at the tumor, as shown in table III. Compared to intact B72.3, the modified B72.3 produced lower blood activity (1.1% ID/g) and higher tumor activity ((6.02% ID/g) at 4 days.

Figure 13:
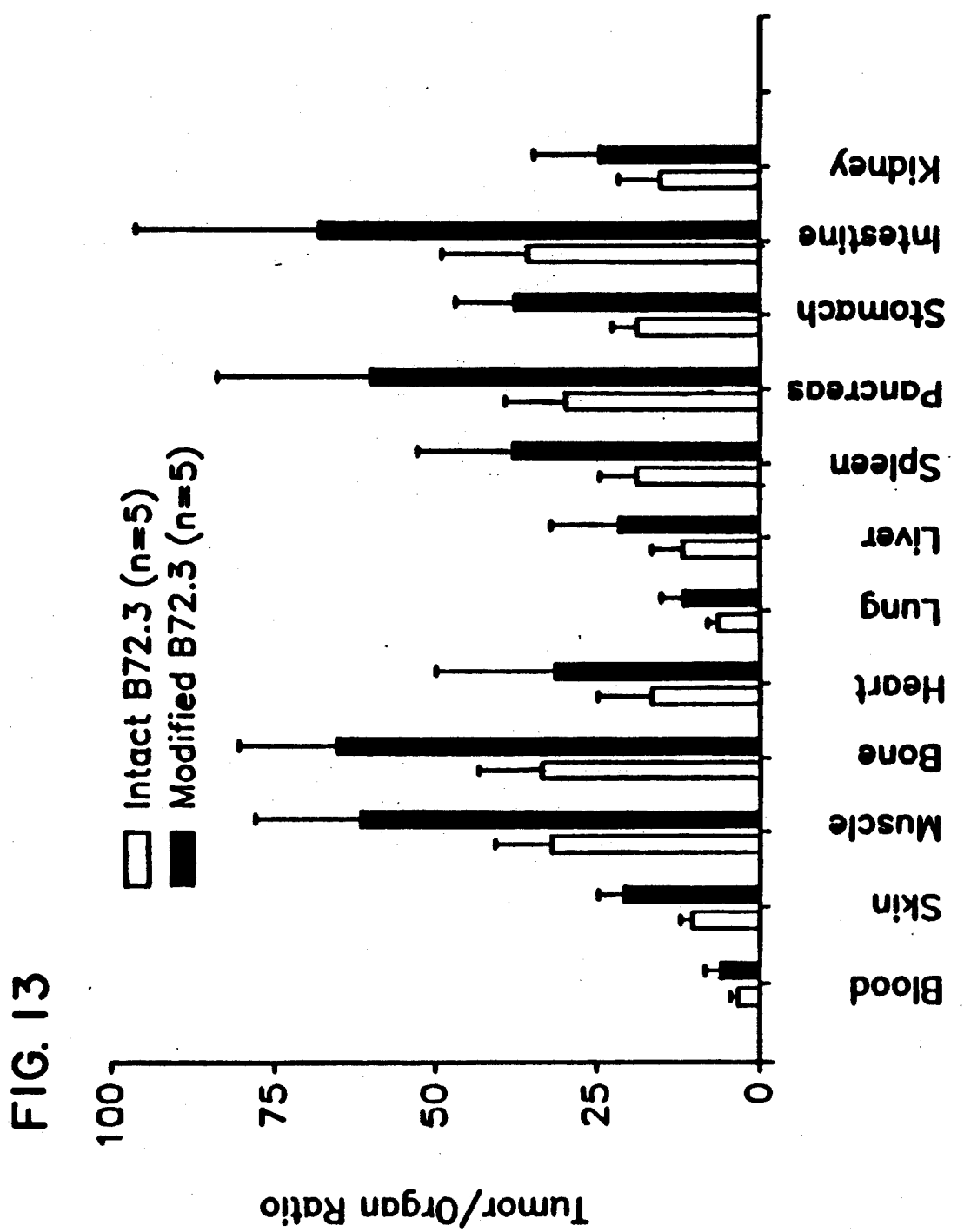
FIG. 13 shows the biodistribution as tumor/organ ratio of MAb's B72.3 and Modified B72.3 in LS174T colon carcinoma-bearing nude mice four days after injection.
Figure 14:
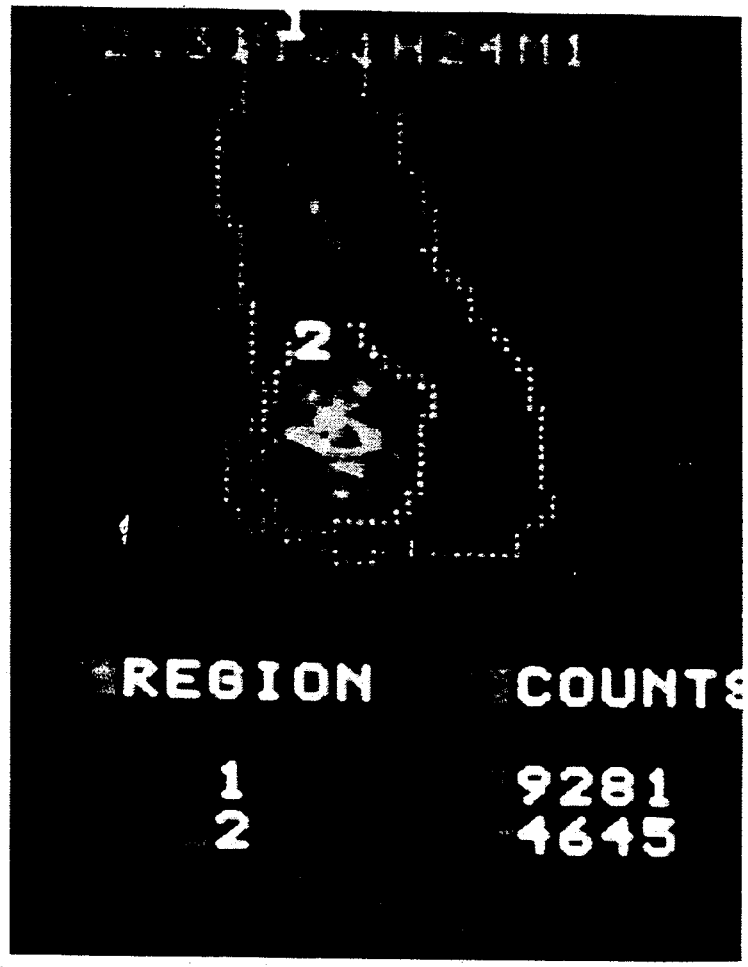
FIG. 14 shows the image obtained on day 1 after injection of I-131 labeled modified B72.3.

As can be seen in FIG. 13, all of the various organ activities were higher for the modified B72.3, except kidney, as expected for a more rapidly cleared antibody. Thus, as shown in FIG. 14, the tumor to organ ratio for modified B72.3 was significantly higher than the corresponding ratios for the intact B72.3. The tumor to organ ratio was even improved for kidney due to the higher activity of the modified antibody at the tumor site.

EXAMPLE 17

Imaging of B72.3 in Tumor Bearing Mice

Figure 15:
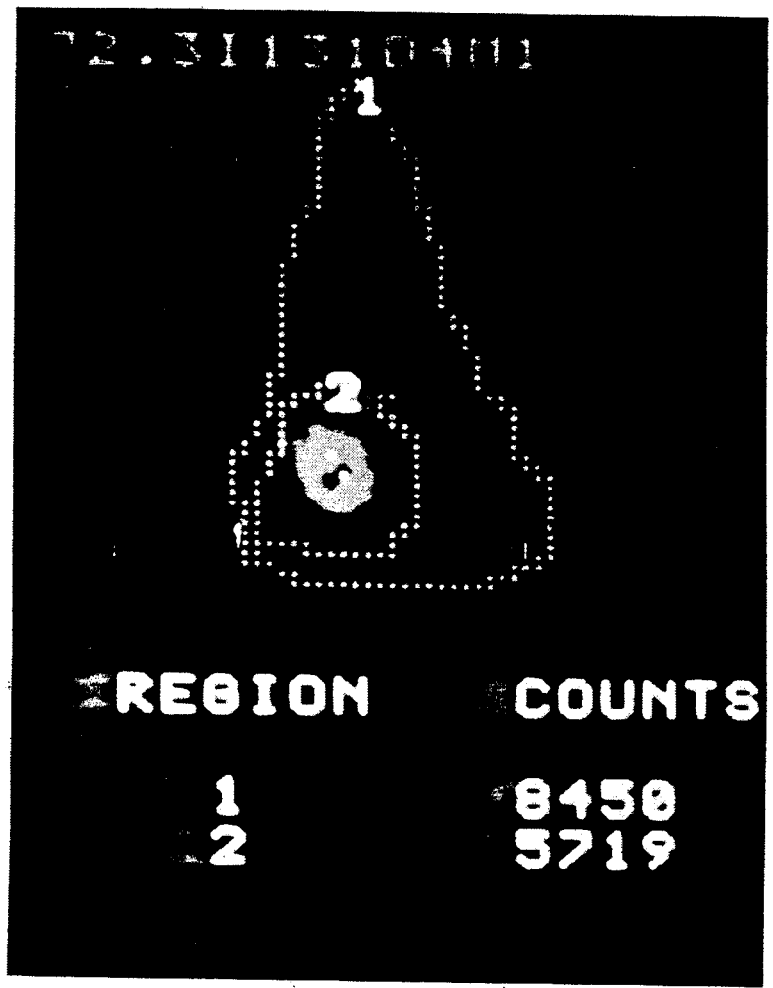
FIG. 15 shows the image obtained on day 4 after injection of I-131 labeled modified B72.3.

Image analysis of LS174T tumor-bearing mice injected with modified B72.3 provided an estimate of tumor/whole antibody distribution after injection. FIG. 14 shows an immunoscintograph at day after injection. The image shows a clear definition of the tumor with little background radioactivity. FIG. 15 shows an immunoscintograph at 4 days after injection. By 4 days, the tumor was clearly seen with little radioactivity remaining in the blood pool of the animal. Results were similar for all animals.

Thus, the modified B72.3 was found to be very useful in obtaining high quality immunoscintographs within a short time of injection of tumors reactive with B72.3.

TNT-1 is an IgG$_{2a}$ monoclonal antibody which utilize necrotic tumor as a target for their selective binding to human cancers. We modified this antibody with on average one PDP group per molecule as in Example 1, and analyzed whole body retention time as shown in Example 18.

EXAMPLE 18

Use of Monoclonal Antibody TNT-1

Figure 16:
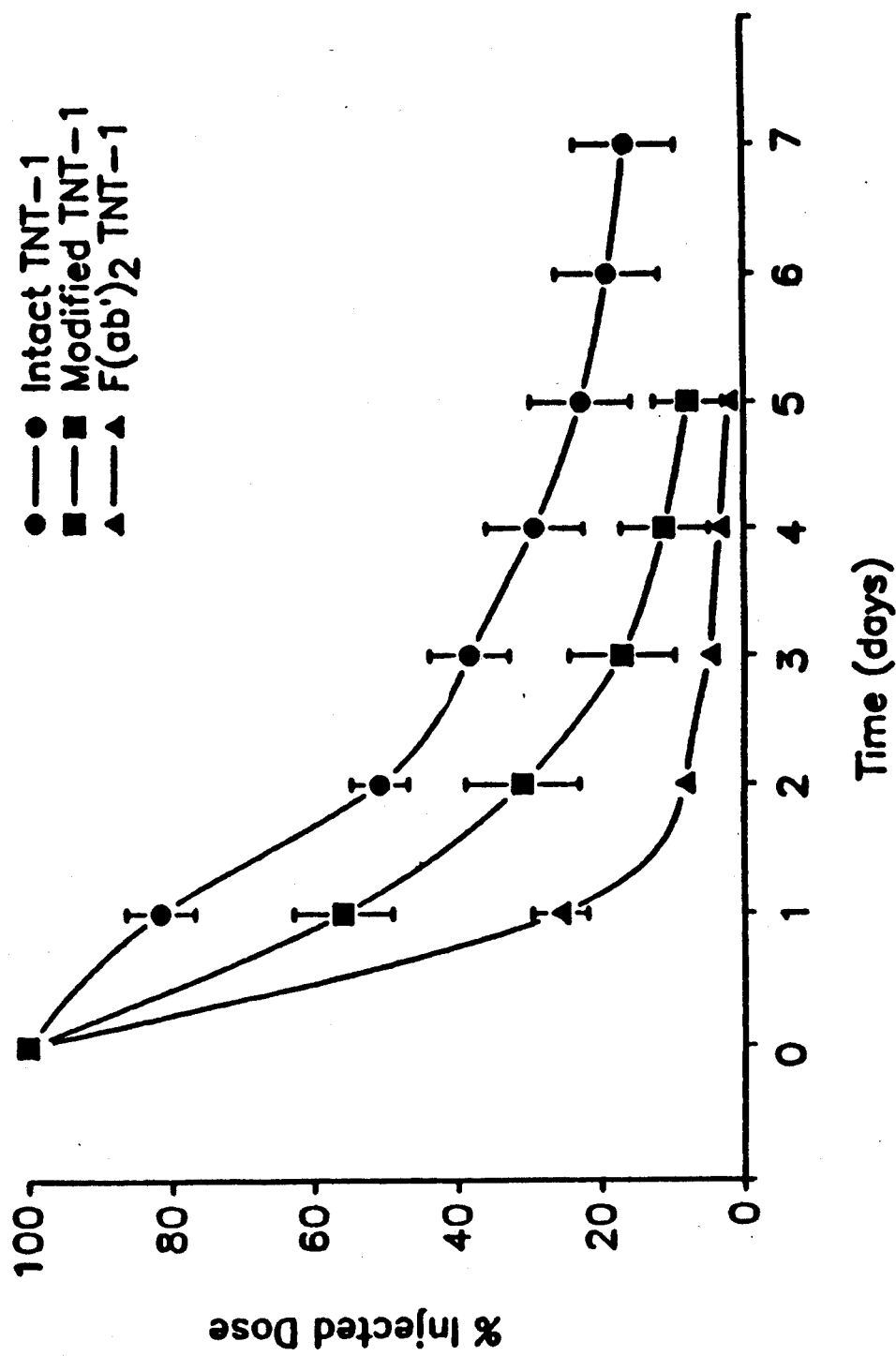
FIG. 16 shows the whole body retention of different preparations of radiolabeled MAb's TNT-1 in athymic nude mice.

We obtained TNT-1 as in Epstein, A.L. et al., A Novel Method for the Detection of Necrotic Lesions in Human Cancer, *Cancer Res.* 48:5842-5848 (1988), the disclosure of which is hereby incorporated by reference. The TNT-1 MAb's were radiolabeled by the method of Example 3. Total body clearance times were measured as in Example 10. FIG. 16 shows the results of these total body clearance experiments. The modified TNT-1 MAb's showed a decrease in whole body half-time clearance time relative to intact TNT-1, and an increase relative to the F(ab')$_2$ fragments of TNT-1.

Thus, the modified TNT-1 behaved similarly to the other modified antibodies. We, therefore, expect, that the utility of the modified TNT-1 MAb's to be equivalent to the other modified antibodies tested.

Accordingly, we believe that modifications to any antibody using the methods of the present invention will provide improved tumor imaging. In order to produce an image of any desired tissue type using the methods of the present invention, antibodies to that tissue type must first be obtained. Polyclonal antibodies can be obtained in a conventional manner as will be known by one of skill in the art. Alternatively, monoclonal antibodies can be prepared in order to obtain the increased specificity provided by these antibodies, as will also be known by one of skill in the art. The antibodies are then chemically conjugated with a heterobifunctional agent. After conjugation, a suitable label is applied to the modified antibodies.

Although the foregoing examples make use of imaging of a label comprising a gamma radiation emitting radionuclide, many other label types and imaging systems are contemplated within the scope of the present invention. For example, radio-opaque materials, such as barium, cesium or iodine can be imaged using conventional X-rays. Paramagnetic or supermagnetic particles can be used as labels, using MRI imaging technology to produce an image of the location of the antibodies. Additionally, technicium can be used as label. These alternative labels may be conjugated to the modified antibodies using conventional methods.

The labeled antibodies can be included in pharmaceutical preparations for the introduction of label into a subject including pharmaceutically acceptable excipients, carriers, or bases. Suitable excipients, carriers, or bases include saline, phosphate buffered saline, glycerol, calcium carbonate, and the like. These compositions are then introduced through any of a variety of means, such as local injection, intra-venous injection, or oral administration in cases where reduced signal strength is required or where imaging of tissue in the oral cavity are desired. However, preferably, administration is through systemic injection in order to maximize exposure of the targeted tissue to the antibody.

We believe that modification to antibodies by the addition of one or more PDP groups in accordance with the present invention will produce significantly improved results when these modified antibodies are incorporated into an immunotherapeutic agent. Such therapeutic agents generally comprise an antibody specific to a tumor or other diseased tissue combined with one or more biologically active molecules. Suitable biologically active molecules which function in such agents are toxins, such as the diphtheria toxin (ricin) A-chain or any of a variety of plant toxins known by those of skill in the art; radionuclides, such as radioactive isotopes of yttrium, iodine, phosphorus, and other commonly used radiotherapeutic agents; drugs, such as methotrexate, 5-fluorouracil, or adriamycin; chelates, including EDTA and EGTA; cis-platinum and other toxic organo-metallic agents, and any other therapeutic agent.

Heretofore, the promise of effective immunotherapy has yet to be fully realized. We believe that the increased activity and specificity of the modified antibodies of the present invention will produce immunotherapeutic agents having sufficient activity and specificity for their target tissues to overcome the deficiencies of prior immunotherapeutic agents. Thus, target disease tissues can be killed without significantly affecting the healthy tissues of the subject, when the subject is injected with the appropriate immunotherapeutic agent.

In the use of these immunotherapeutic agents, antibodies specific to particular undesired tissue types must first be obtained. If the desired antibodies are not available, the antibodies may be raised in a suitable organism by injecting the organism with antigens and obtaining serum from the mammal, as will be known by one of skill in the art. Alternatively, and preferably, monoclonal antibodies can be raised in a manner known to one of skill in the art. The antibodies are then chemically conjugated with a heterobifunctional agent. After conjugation, the resulting modified antibodies are further modified by conjugation with a biologically active agent, such as a therapeutic agent described above. The antibodies are combined into pharmaceutical compositions containing a pharmaceutically acceptable carrier, excipient or base. Such pharmaceutically acceptable carriers, excipients, or bases include normal saline for systemic injection, glycerol, calcium carbonate. The compositions are then ready for introduction into a patient, such as a mammal.

The antibodies are then introduced into the subject via any known administration route. For example, the compositions can be introduced through systemic injection, local injection into the affected tissue, can be applied topically to externally affected tissue, and can be taken orally in cases where reduced signal strength is required or where therapy of tissue in the oral cavity are desired.

Dosage of the biologically active agent containing antibody will depend on target tissue sensitivity to the toxin, the amount of affected tissue, route of administration, the affinity of the antibody, clearance rates and on other factors. However, representative dosages will generally be in the range from 1 µg/kg total body mass to 1 mg/kg. In most applications, the dose will preferably be from 5 to 200 µg/kg.

The following example is illustrative of an immunotherapy effective against Raji tumors in mice.

EXAMPLE 19

Treatment of Raji Tumors in Mice

PDP-modified Lym-1 is obtained as in Example 1. The modified antibody is then treated to introduce, on average, one ricin A-chain per antibody molecule. Intact Lym-1 and F(ab')$_2$ fragments are similarly combined with toxin.

Twenty-five mice are divided into five groups. Group I receives intraperitoneal injections at 10 μg/kg total body weight of the ricin-PDP-modified Lym-1 in phosphate buffered saline (PBS) once per week for 8 weeks. Group II receives injections of an equivalent amount ricin-intact Lym-1. Group III receives equivalent amounts of ricin-F(ab')$_2$ fragments of Lym-1. Group IV receives an equivalent amount of unconjugated ricin. Group V receives PBS alone.

After 8 weeks, immunoscintography of all surviving mice using the method of Example 14 is performed. The Group I mice show reduced visualization of tumor compared to any of the other groups. Surviving Group II and Group III mice show some improvement, though less dramatic than the Group I mice. Group IV mice become very ill or die.

Thus, Example 19 shows one particular treatment of a tumor using the modified antibodies of the present invention. Example 19 shows the superior results achieved when using the PDP-modified antibodies of the present invention. Substituting the use of other antibodies specific to other tumors or diseased tissues in mice or other mammals, such as humans, is believed to produce similarly effective results in treating those specific tumors or diseased tissues. Moreover, the substitution of other know toxins is believed to also produce similarly effective results. Example 20 shows the use of a similar therapy effective against pancreatic cancer in humans.

EXAMPLE 20

Treatment of Human Pancreatic Cancer

A monoclonal antibody is obtained which is specific to an antigen found in human pancreatic tumors. This antibody is modified by conjugation to, on average, one PDP group per antibody molecule, as in Example 1. Methotrexate is then conjugated to these modified antibodies as described for Ricin in Example 19.

Two groups of ten pancreatic cancer patients are treated. The first group receives intravenous injections of the drug-PDP-MAb in PBS at 20 μg/kg total body weight on a weekly basis in combination with traditional therapy. The second, group receives injections of PBS in combination with traditional therapy as a control. After 10 weeks, immunoscintography of the surviving patients is performed.

On immunoscintography, the average size of the tumors imaged in the first group of patients is reduced relative to the control group.

Thus, the foregoing example illustrates the utility of the modified antibodies in immunotherapy in humans.

As described above, in one preferred form of the present invention, the modified antibodies are formulated into pharmaceutical compositions. Thus, the PDP-modified antibodies which are conjugated with a drug for immunotherapy may be incorporated into an injectable composition having a cytotoxicly effective amount of the modified antibody-toxin conjugates of the present invention. The following is an example of a cytotoxicly effective composition effective against B-cell lymphomas in humans.

EXAMPLE 21

A Pharmaceutical Composition Effective Against B-Cell Lymphoma in Humans 10 mg/ml Modified radiolabeled Lym-1 from Example 18 Balance Phosphate Buffered Saline (0.9%)

Additionally, the radiolabeled modified MAb's may be formulated into compositions effective to visualize their specific antigens in immunoscintography. The following is one example of such a composition.

EXAMPLE 22

A Pharmaceutical Composition Effective in Immunoscintography of Colon Carcinoma 10 mg/ml Modified radiolabeled B72.3 from Example 15 Balance Phosphate Buffered Saline (0.9%)

It will be appreciated that certain mechanical or chemical variations may suggest themselves to those skilled in the art. The foregoing examples and detailed description are to be clearly understood as given by way of illustration, the spirit and scope of this invention being limited solely by the appended claims.

We claim:

1. An antibody having a first moiety attached thereto at a first attachment site, said first moiety being a heterobifunctional reagent, said antibody also having a radionuclide attached at a second attachment site, said second attachment site being a different site on said antibody than said first attachment site, and said second attachment site not having an attached heterobifunctional reagent of the same type as said first moiety.

2. The antibody of claim 1, wherein said heterobifunctional reagent is selected from the group consisting of SASD, SAND, sulfo-SADP and Traut's Reagent.

3. The antibody of claim 1, wherein said heterobifunctional reagent is SPDP.

4. The antibody of claim 1, wherein said antibodies are monoclonal antibodies, human antibodies, genetically engineered antibodies, chimeric antibodies, synthesized antibodies or polyclonal antibodies.

5. The antibody of claim 1, wherein said antibodies have an in vivo clearance rate between the clearance rates of F(ab')$_2$ fragments and intact antibodies of the same type.

6. The antibody of claim 1 wherein the heterobifunctional reagent is a PDP group.

7. The antibodies of claim 1, wherein there are, on average, one PDP group per antibody molecule.

8. Monoclonal antibody Lym-1 modified at a first attachment site by a first moiety comprising a heterobifunctional reagent and at a second attachment site by a radionuclide, said second attachment site being a different site on said antibody than said first attachment site, and said second attachment site not having an attached heterobifunctional reagent of the same type as said first moiety.

9. Monoclonal antibody TNT-1 modified at a first attachment site by a first moiety comprising a heterobifunctional reagent and at a second attachment site by a radionuclide, said second attachment site being a different site on said antibody than said first attachment site, and said second attachment site not having an attached heterobifunctional reagent of the same type as said first moiety.

10. Monoclonal antibody B72.3 modified at a first attachment site by a first moiety comprising a heterobifunctional reagent and at a second attachment site by a radionuclide, said second attachment site being a different site on said antibody than said first attachment site, and said second attachment site not having an attached heterobifunctional reagent of the same type as said first moiety.

11. A method of improving the activity and specificity of antibodies, and providing enhanced in vivo clearance thereto, said method comprising the following steps in any order:

chemically conjugating a first moiety to said antibodies at a first attachment site, said first moiety being a heterobifunctional agent; and attaching a radionuclide to said antibodies at a second attachment site, said second attachment site being a different site on said antibody than said first attachment site, and said second attachment site not having an attached heterobifunctional reagent of the same type as said first moiety.

12. The method of claim 11, wherein the chemically conjugating step comprises conjugating with SPDP.

13. The method of claim 12, wherein the chemically conjugating step comprises conjugation with on average one PDP group per antibody molecule.

* * * * *